(12) United States Patent
Torres et al.

(10) Patent No.: US 11,304,682 B2
(45) Date of Patent: Apr. 19, 2022

(54) NON-INVASIVE ESTIMATION OF THE MECHANICAL PROPERTIES OF THE HEART

(71) Applicants: University of South Carolina, Columbia, SC (US); The United States Government as Represented by the Department of Veterans Affairs, Washington, DC (US)

(72) Inventors: William M. Torres, Philadelphia, PA (US); Francis G. Spinale, Blythewood, SC (US); Tarek M. Shazly, Columbia, SC (US)

(73) Assignee: University of South Carolina, Columbia, SC (US)

( * ) Notice: Subject to any disclaimer, the term of this patent is extended or adjusted under 35 U.S.C. 154(b) by 349 days.

(21) Appl. No.: 16/524,380

(22) Filed: Jul. 29, 2019

(65) Prior Publication Data

US 2020/0100768 A1 Apr. 2, 2020

Related U.S. Application Data

(60) Provisional application No. 62/738,014, filed on Sep. 28, 2018.

(51) Int. Cl.
*A61B 8/08* (2006.01)
*G06T 17/20* (2006.01)

(52) U.S. Cl.
CPC .......... *A61B 8/5223* (2013.01); *A61B 8/0883* (2013.01); *A61B 8/485* (2013.01); *G06T 17/20* (2013.01); *G06T 2210/41* (2013.01)

(58) Field of Classification Search
CPC ..... A61B 8/5223; A61B 8/0883; A61B 8/485; G06T 17/20; G06T 2210/41
See application file for complete search history.

(56) References Cited

U.S. PATENT DOCUMENTS

2016/0249880 A1* 9/2016 Konofagou .......... A61B 8/0883
600/438

OTHER PUBLICATIONS

Hassaballah, Abdallah I., Mohsen A. Hassan, Azizi N. Mardi, and Mohd Hamdi. "An inverse finite element method for determining the tissue compressibility of human left ventricular wall during the cardiac cycle." Plos One 8, No. 12 (2013): e82703.*
Kattan, Peter I. "The Linear Brick (Solid) Element." In MATLAB Guide to Finite Elements, pp. 367-396. Springer, Berlin, Heidelberg, 2008.*
Krishnamurthy, Adarsh, Christopher T. Villongco, Joyce Chuang, Lawrence R. Frank, Vishal Nigam, Ernest Belezzuoli, Paul Stark et al. "Patient-specific models of cardiac biomechanics." Journal of computational physics 244 (2013): 4-21.*

* cited by examiner

*Primary Examiner* — Carolyn A Pehlke
(74) *Attorney, Agent, or Firm* — Burr & Forman LLP; Douglas L. Lineber

(57) ABSTRACT

Methods and systems for utilizing myocardial strain imaging in an inverse framework to identify mechanical properties of the heart and to determine structural and functional milestones for the development and progression to heart failure.

8 Claims, 17 Drawing Sheets

Table 1: Echocardiographic estimation of indices of geometry and function.

| Treatment | Day | LVEF (%) | EDV/BW (mL/kg) | LA Area (cm$^2$) |
|---|---|---|---|---|
| Baseline (17) | 0 | 64.6 ± 1.3 | 1.6 ± 0.1 | 6.2 ± 0.3 |
| HFrEF (8) | 14 | 37.8 ± 2.3* | 2.8 ± 0.2* | 10.1 ± 0.4* |
|  | 28 | 37.5 ± 3.4* | 2.6 ± 0.2* | 11.0 ± 0.4* |
| HFpEF (9) | 14 | 63.8 ± 1.0 | 1.6 ± 0.2 | 9.9 ± 0.5* |
|  | 28 | 66.1 ± 1.0 | 1.5 ± 0.1 | 11.3 ± 0.5* |

Values are means ± SE. * $p<0.05$ vs. the respective baseline value. (LVEF: left ventricular ejection fraction; EDV: end-diastolic volume; BW: body weight; LA: left atrium)

FIGURE 12

NON-INVASIVE ESTIMATION OF THE MECHANICAL PROPERTIES OF THE HEART

This invention was made with government support under 3R01HL130972-01A1S1 awarded by the National Heart, Lung, and Blood Institute of the National Institutes of Health. The government has certain rights in the invention.

BACKGROUND OF THE INVENTION

1) Field of the Invention

The present invention relates to utilizing myocardial strain imaging in an inverse framework to identify mechanical properties of the heart.

2) Description of Related Art

Heart failure (HF) is a clinical syndrome which most commonly arises from two potentially overlapping physiological causes: impaired left ventricular (LV) ejection performance or impaired LV filling. In terms of HF phenotyping, impaired LV ejection performance is defined as HF with reduced ejection fraction (HFrEF) while impaired LV filling with a stable ejection performance is defined as HF with preserved ejection fraction (HFpEF). These HF phenotypes emerge from distinctly different etiologies, whereby HFrEF commonly occurs secondary to myocardial injury/ischemia and HFpEF arises from a chronic LV pressure overload such as hypertension. In both HFrEF and HFpEF, the LV undergoes progressive changes in geometry, composition, and mechanical properties collectively known as LV remodeling. While nominally an adaptive response, LV remodeling underlies HF progression, and consequently its serial assessment holds great value in HF diagnosis and prognosis.

Although commonly used in a clinical setting, global measures of LV function such as ejection fraction or volumes can be insensitive to early changes in LV performance and thus fail to identify HF development and progression. Alternatively, the assessment of regional function through the quantification of LV myocardial strain, defined as the fractional change in length of a myocardial segment relative to its baseline length, has gained traction recently as a comparatively sensitive index of LV remodeling. Developments in ultrasound-based imaging technology enable serial quantification of LV myocardial strain in a clinical setting. Specifically, speckle-tracking echocardiography (STE) tracks segmental length changes via the relative movement of intrinsic acoustic markers to quantify regional LV myocardial strain]. The analysis of both global (fractional change in total segmental length) and regional longitudinal strain using STE can provide diagnostic information in disease states ranging from myocardial infarction to cardiotoxicity.

Despite the demonstrated clinical utility of STE for the assessment of LV remodeling, there are clear factors limiting its clinical adoption. Firstly, most clinical use of STE has been focused on global longitudinal strain despite the availability of regional measures—significantly narrowing the field of diagnostic information by masking potentially distinct regional changes. Secondly, obtained strain measurements are highly dependent on hemodynamics (e.g. blood pressure, heart rate) and assumptions used to calculate LV wall geometry. Not fully accounting for these factors diminishes the value of serial STE-based measurements and inter-subject comparisons.

In response to the abrupt (e.g. myocardial infarction) or insidious (e.g. prolonged pressure overload) onset of myocardial injury, the left ventricle (LV) undergoes changes in geometry, composition, and mechanical properties, collectively known as LV remodeling. While nominally an adaptive response, it is generally accepted that progressive LV remodeling underlies the progression to heart failure in various forms of heart disease. Heart failure, a clinical syndrome resulting in impairment of ventricular filling or the ejection of blood, is the leading cause of morbidity and mortality across the world. This syndrome presents a distinct challenge to healthcare providers in terms of diagnosis and management as it can arise from a multitude of pathologies which present in various hallmarks and disease phenotypes. To that end, sensitive non-invasive techniques to track the rate and extent of LV remodeling are warranted.

Left ventricular remodeling, a mechanistic response to myocardial injury, has been shown to underlie the progression to heart failure. As such, sensitive techniques to track the rate and extent of remodeling are necessary to evaluate risk and treatment options on a patient-specific basis. Echocardiography has become the gold standard for assessing the structure and function of the heart.

Accordingly, it is an object of the present invention to utilize recent advancements in both hardware and software for a relatively new echocardiographic capability: the assessment of regional myocardial deformation through two-dimensional speckle tracking echocardiography. While this capability has been shown to be clinically useful in a variety of disease cases, a dependency on hemodynamic load and left ventricular geometry has diminished its widespread clinical utility. Sensitive techniques to track the rate and extent of left ventricular remodeling are necessary to evaluate risk and treatment options on a patient-specific basis. The current disclosure has developed a novel extension to speckle-tracking echocardiography technology as a means to non-invasively identify the mechanical properties of the left ventricular myocardium. This technology can be implemented as a post-processing compliment to traditional echocardiographic studies to provide a detailed biomechanical analysis of the changing heart as it pertains to disease progression.

BRIEF DESCRIPTION OF THE DRAWINGS

The construction designed to carry out the invention will hereinafter be described, together with other features thereof. The invention will be more readily understood from a reading of the following specification and by reference to the accompanying drawings forming a part thereof, wherein an example of the invention is shown and wherein:

FIG. 12 shows Table 1.

Figure 1:
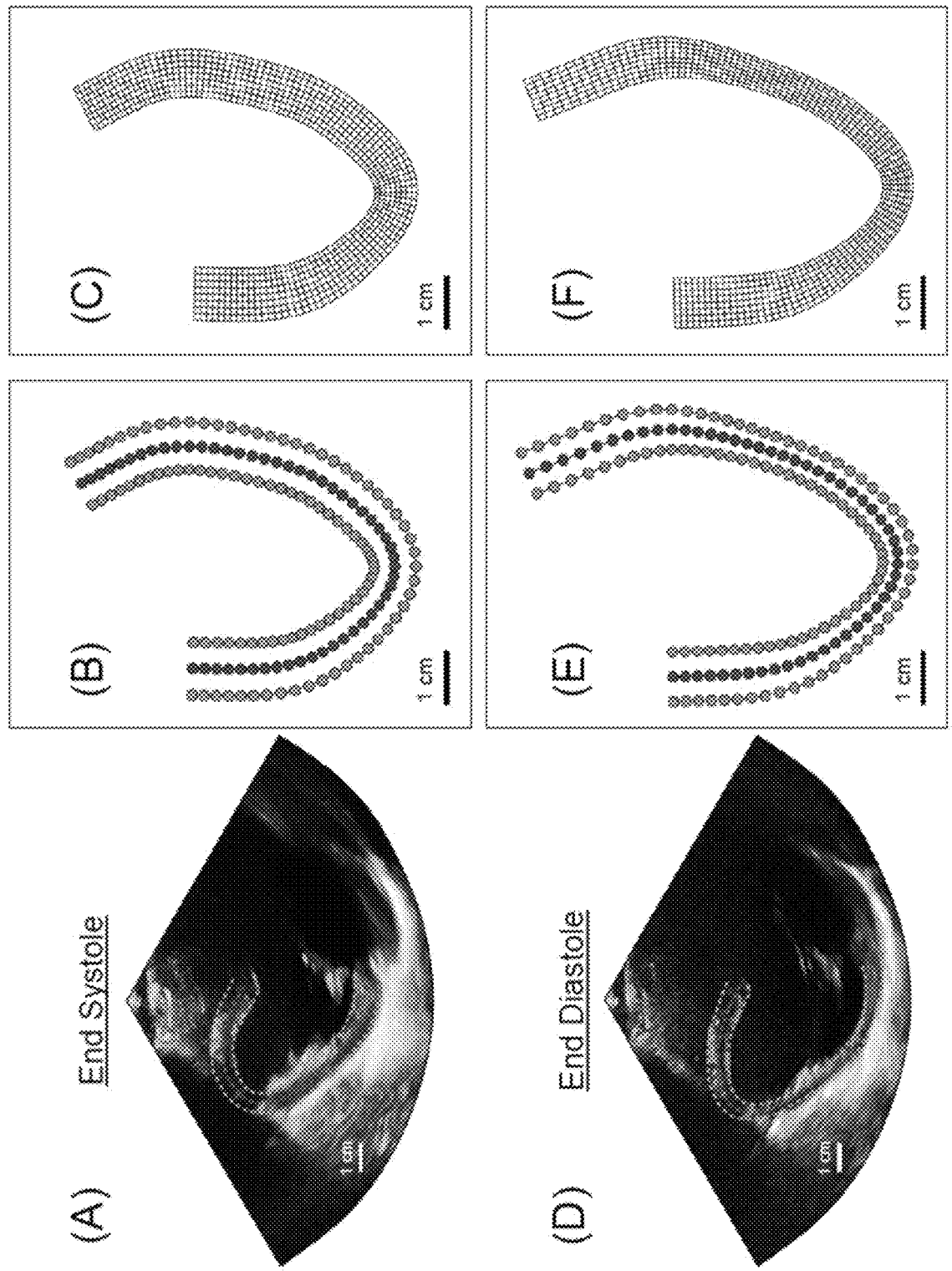
FIG. 1 shows reference geometry composed of a monolayer of eight-node trilinear hexahedral elements with two elements spanning the distance between each of the mid-myocardial nodes and eight elements spanning the distance between the pairs of endocardial and epicardial nodes.

It will be understood by those skilled in the art that one or more aspects of this invention can meet certain objectives, while one or more other aspects can meet certain other objectives. Each objective may not apply equally, in all its respects, to every aspect of this invention. As such, the preceding objects can be viewed in the alternative with respect to any one aspect of this invention. These and other objects and features of the invention will become more fully apparent when the following detailed description is read in conjunction with the accompanying figures and examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art. Such objects, features, benefits and advantages will be apparent from the above in conjunction with the accompanying examples, data, figures and all reasonable inferences to be drawn therefrom, alone or with consideration of the references incorporated herein.

DETAILED DESCRIPTION OF A PREFERRED EMBODIMENT

With reference to the drawings, the invention will now be described in more detail. Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are herein described.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

The methodology disclosed herein describes a novel and non-obvious extension of the two-dimensional speckle tracking technology to allow for the definition of a constitutive relation for the regional left ventricular myocardium that links the states of stress and strain, effectively removing the dependency on hemodynamics and geometry. An inverse finite element analysis technique was employed with a pattern search optimization algorithm to identify an optimal distribution of mechanical properties necessary to match in-silico regional strains, average wall thicknesses, and left ventricular area with those experimentally measured in-vivo. After minimization of this unique objective function, it is possible to then visualize the heterogeneous two-dimensional distribution of mechanical properties across the left ventricle and compute/display both radial and longitudinal end-diastolic wall stress. This technology would allow for a comprehensive biomechanical analysis of the left ventricle to be performed in a clinical setting for the assessment of the rate and extent of myocardial remodeling in response to heart disease.

This technology will be used as a compliment to standard echocardiographic analysis as a sensitive biomechanical marker of the rate and extent of left ventricular remodeling. This analysis can be completed as a post-processing step from images that are routinely acquired in a complete transthoracic echocardiographic study.

Background and Significance.

At present, echocardiography is the most clinically-accessible modality to assess changes in the structure and function of the heart. A recent review demonstrated that an echocardiographic study was conducted on over 2% of all hospitalizations and that the average number of echocardiograms performed annually has steadily risen approximately 3% year-over-year after adjustment of population growth. See, Okrah K, Vaughan-Sarrazin M, Cram P. Trends in echocardiography utilization in the Veterans Administration Healthcare System. 2015; 91:165-171 and Papolos A, Narula J, Bavishi C, Chaudhry F A, Sengupta P P. U.S. Hospital Use of Echocardiography: Insights From the Nationwide Inpatient Sample. J Am Coll Cardiol. 2016; 67:502-511.

Echocardiography has been shown to be a reliable, reproducible, and safe platform to perform a variety of analyses on the myocardium, pericardium, and valvular structures. LV ejection fraction (LVEF), for example, is the most common metric of cardiac performance in clinical practice. However, only 50% of patients diagnosed with heart failure present with a reduced LVEF (LVEF below 45%). See Id. Moreover, this measurement is an estimate of global systolic function and is subject to error imposed by the geometric assumptions underlying the volumetric calculations and a dependency on load. See, Argulian E, Chandrashekhar Y, Shah S J, Huttin O, Pitt B, Zannad F, Bonow R O, Narula J. Teasing Apart Heart Failure with Preserved Ejection Fraction Phenotypes with Echocardiographic Imaging: Potential Approach to Research and Clinical Practice. Circ Res. 2018; 122:23-25.

Alternatively, speckle-tracking echocardiography (STE), an ultrasound-based technique which tracks the movement of intrinsic acoustic markers of the LV to quantify myocardial deformation, has gained traction recently as a sensitive index of remodeling. Two-dimensional longitudinal strain as quantified through STE has been shown to be an accurate measurement of regional longitudinal deformation that provides unique diagnostic information in a variety of disease states with the added benefit of being independent of tethering and global cardiac translation. While this technology has a wide field of clinical applications from myocardial infarction to cardiotoxicity, there are various factors impeding its widespread clinical adoption. Chief among these, strain has been shown to be highly dependent on hemodynamics (e.g. blood pressure, heart rate) and LV geometry (e.g. LV chamber size, wall thickness).

To that end, the primary motivation behind the technology presented in the current disclosure is to non-invasively quantify the local mechanical properties of the left ventricular myocardium, effectively removing the dependency on LV hemodynamics/geometry and potentially providing a more sensitive response variable to track the progression of LV remodeling. Given the fact that the regional deformation as assessed from STE is known and there is a basis to estimate the mechanical load (i.e. ventricular pressure), there is sufficient information to formulate an inverse boundary value problem within the framework of continuum mechanics and the theory of finite elasticity. The proposed technology will allow for the identification of a novel index of regional mechanical stiffness as a marker of LV remodeling and the progression of heart failure.

Methodology.

Acquisition of Patient-Specific Data.

Transthoracic echocardiographic studies were performed (GE VIVID E9 with XDCLEAR Ultrasound System; M5S (1.5-4.6 MHz) transthoracic transducer probe) and digital images were transferred to a workstation (ECHOPAC, VINGMED, GE) for post-processing. Cardiac dimensions were assessed by two-dimensional echocardiographic studies. For each digital loop, a region of interest (ROI) was defined at the onset of the R-wave by manually identifying the endocardial and epicardial borders. The ROI was then discretized with a spatial mesh of acoustic clusters to be tracked on a frame-to-frame basis throughout a single cardiac cycle.

Quantitative strain analysis (Q-analysis) was performed, regional tracking quality was assessed, and the ROI was manually adjusted by the operator to improve tracking quality where necessary. Subsequently, spatial coordinates of the mid-myocardial nodes were exported for each frame of the digital loop. Additionally, wall thickness was collected at early- and end-diastole for each of the six conventional echocardiographic segments (basal posterior, mid posterior, apical posterior, apical anterior septum, mid anterior septum, and basal anterior septum). Finally, pulse-wave Doppler, using a sample volume placed at the tips of the mitral valve leaflets, was used to determine the peak early mitral inflow velocity (E) while tissue Doppler assessment was used to calculate the peak early mitral annular velocity (E') with a sample volume positioned at the lateral site of the mitral annulus. Pulmonary capillary wedge pressure (PCWP) was subsequently calculated using the method proposed by Nagueh et al in 1997.28

Formulation of the Finite-Element Mesh.

The initial, unloaded, configuration was generated from the position of the mid-myocardial nodes at the onset of diastole, the point at which the cross-sectional area was at a minimum. For each mid-myocardial node, a thickness was defined by computing a cubic spline interpolation between the known thicknesses at the onset of diastole of the six echocardiographic segments. Endocardial and epicardial nodes were subsequently generated based on the position of the mid-myocardial nodes and estimated thicknesses. The finite-element mesh was constructed from this reference geometry composed of a monolayer of eight-node trilinear hexahedral elements with two elements spanning the distance between each of the mid-myocardial nodes and eight elements spanning the distance between the pairs of endocardial and epicardial nodes, see FIG. 1 (A)-(C). This process was also completed for the end-diastolic configuration for comparative purposes and calculation of the objective function which will be elaborated upon in subsequent sections, see FIG. 1 (D)-(F).

Material Model and Boundary Conditions.

The left ventricular myocardium is modeled with a transversely isotropic Mooney-Rivlin constitutive model, a model well-suited for biological soft tissues with a single preferred fiber direction. The uncoupled strain energy function is:

$$W = F_1(\tilde{I}_1, \tilde{I}_2) + F_2(\tilde{\lambda}) + \frac{K}{2}[\ln(J)]^2. \quad (1)$$

Here, the coefficient is the bulk modulus-like penalty parameter and is the determinant of the deformation gradient tensor. The function $F_1(\tilde{I}_1, \tilde{I}_2)$, a function of the first and second invariants of the deviatoric right Cauchy-Green deformation tensor, represents the material response of the isotropic Mooney-Rivlin ground substance matrix of the form:

$$F_1(\tilde{I}_1, \tilde{I}_2) = S[C_1(\tilde{I}_1 - 3)] + S[C_2(\tilde{I}_2 - 3)] + \frac{K}{2}[\ln(J)]^2 \quad (2)$$

where $C_1$ and $C_2$ are the Mooney-Rivlin material coefficients and S is the regional stiffness index. $F_2(\tilde{\lambda})$, a function of the fiber stretch ratio, represents the contribution from the fiber family with a strain energy of the following form:

$$F_2(\tilde{\lambda}) = \begin{cases} 0 & \tilde{\lambda} \leq 1 \\ C_3\left[e^{-C_4}\left(Ei(C_4\tilde{\lambda}) - Ei(C_4)\right) - \ln\tilde{\lambda}\right] & 1 < \tilde{\lambda} < \lambda_m \\ C_5(\tilde{\lambda} - 1) + C_6\ln\tilde{\lambda} & \tilde{\lambda} \geq \lambda_m \end{cases} \quad (3)$$

where $C_3$ scales the exponential stresses, $C_4$ is the fiber crimping coefficient, $C_5$ is the modulus of the straightened fibers, and $\lambda_m$ is the stretch at which the fibers are straightened. Furthermore, i is the exponential integral function and $C_6$ is determined from stress continuity requirements. The fiber orientation was specified for each element to be 15° relative to the longitudinal axis on the longitudinal-radial plane with a λm of 1.10. The remaining material parameters, barring the regional stiffness index, were chosen from prior work on biaxial testing on excised canine hearts. See, Novak V P, Yin F C P, Humphrey J D. Regional Mechanical Properties of Passive Myocardium. 1994, which is hereby incorporated by reference. The regional stiffness index, S, was determined from the optimization scheme described infra.

Two quasi-static structural mechanics steps were defined. In step one, a prescribed translation was applied to the basal nodes from the undeformed configuration to the expected position at end-diastole as determined from STE. In step two, the basal node positions were fixed, and the end-diastolic pressure was applied to the endocardial surface. The solution was solved for using the PARDISO linear solver within the FEBio application. See, Maas S A, Ellis B J, Ateshian G A, Weiss J A. FEBio: Finite Elements for Biomechanics. J Biomech Eng [Internet]. 2012; 134: 011005. Available from: http://biomechanical.asmedigitalcollection.asme.orgiarticle.aspx?articleid=143139 6, which is hereby incorporated by reference.

Identification of Material Properties.

An objective function (Π) of the form:

$$\Pi = \left(\frac{A' - A}{A} + \sum_{i=1}^{6}\left(\frac{\varepsilon'_i - \varepsilon_i}{\varepsilon_i}\right) + \frac{\bar{t}' - \bar{t}}{\bar{t}}\right) \times 100\% \quad (4)$$

was developed as a function of the actual end-diastolic area (A), regional strain ($\varepsilon_i$) relative to the undeformed mesh, and mean wall thickness ($\bar{t}$) determined from the end-diastolic mesh, see FIG. 1 (F). Additionally, A', εi, and $\bar{t}'$ represent the end-diastolic area, regional strain relative to the undeformed mesh, and mean wall thickness computed from the deformed FE model, respectively. The factors entering the optimization scheme were the stiffness indices (S) defined at the center of each of the six conventional anatomical segments of the LV. A cubic spline interpolation was used to define a continuous distribution of stiffness indices between the six segments. A pattern search optimization algorithm, ideal for the minimization of a non-differentiable objective function, was employed to identify an optimal set of stiffness indices coincident with the global minimum of the objective function. The pattern search algorithm was terminated when a successful poll resulted in a change in the objective function of less than 1E-6, see FIG. 3.

Post-Processing of Results.

Figure 4:
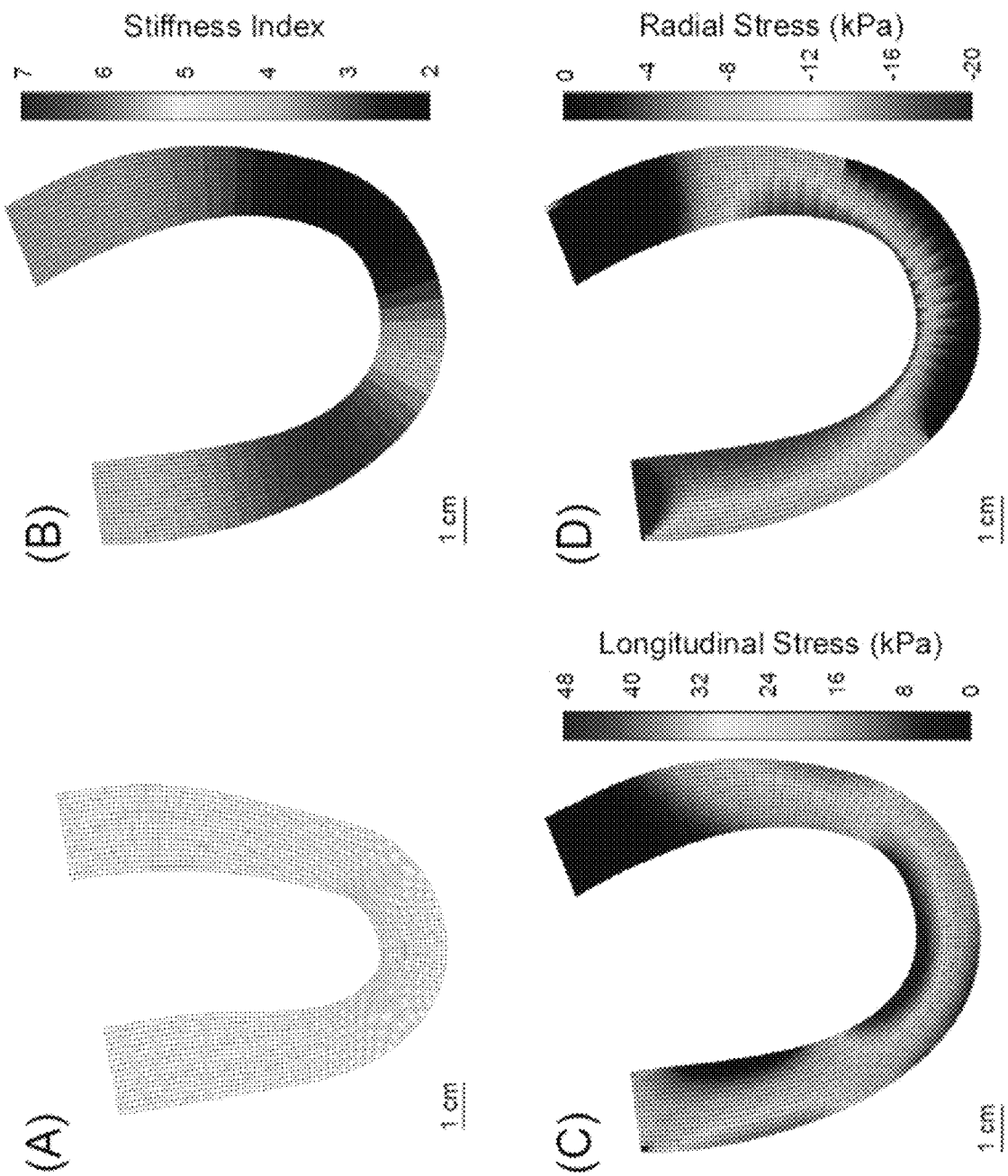
FIG. 4 shows a representative result for a human hypertrophic left ventricle based on the current disclosure.

After optimization was complete, a final simulation with a refined FE mesh, see FIG. 4 (A), was performed and post-processing of the results was initiated. The 2-D Cauchy stress tensor for each element was transformed to represent longitudinal (σ) and radial (σr) stresses after computing the angle (θ) formed by the longitudinal direction in the local coordinate system and the global y-axis:

$$\sigma_l = \frac{\sigma_{xx} + \sigma_{yy}}{2} + \frac{\sigma_{xx} - \sigma_{yy}}{2}\cos 2\theta + \tau_{xy}\sin 2\theta \quad (5)$$

$$\sigma_r = \frac{\sigma_{xx} + \sigma_{yy}}{2} - \frac{\sigma_{xx} - \sigma_{yy}}{2}\cos 2\theta - \tau_{xy}\sin 2\theta \quad (6)$$

where $\sigma_{xx}$ and $\sigma_{yy}$ are the normal stress in the global x-axis and y-axis, respectively, and $\tau_{xy}$ is the shear stress. Colorimetric plots of the stiffness indices, see FIG. 4 (B), longitudinal stress, see FIG. 4(C), and radial stress, see FIG. 4(D), were generated for the end-diastolic deformed geometry.

Summary and Future Directions.

Heart disease has been shown to elicit changes in the mechanical properties of the myocardium which, in turns, plays a role in the feed-forward mechanism responsible for the progression to heart failure. While this consensus exists, the in-vivo estimation of the mechanical properties of the myocardium has been limited to expensive and technically challenging post-processing of magnetic resonance analyses. The present disclosure outlines a methodology and framework which would make it possible to perform an analysis of mechanical properties to track the rate and extent of heart disease progression on every patient presenting with symptoms of heart disease.

While the work presented herein specifically relates to the left ventricle of the heart, the same methodology can be extended to other soft tissues within the body. This extension would be contingent on two factors: (1) access to an image modality which would allow for the successful tracking of the tissue deformation in response to a given load and (2) an accurate estimation of the in-vivo load exerted on the tissue. As an example, thoracic or abdominal aortic aneurysms would be an ideal application for this technology. First, the irregular geometries of these structures negate the use of analytical approaches to identify constitutive model parameters and/or estimate the wall stress distribution. Furthermore, STE and magnetic resonance have been previously applied to the aorta to track the deformation of the aorta during and after ventricular ejection. See, Alreshidan M, Shahmansouri N, Chung J, Lash V, Emmott A, Leask R L, Lachapelle K. Obtaining the biomechanical behavior of ascending aortic aneurysm via the use of novel speckle tracking echocardiography. J Thorac Cardiovasc Surg. 2017; 153:781-788 and Bell V, Mitchell W A, Sigurdsson S, Westenberg J J M, Gotal J D, Torjesen A A, Aspelund T, Launer L J, de Roos A, Gudnason V, Harris T B, Mitchell G F, Longitudinal and circumferential strain of the proximal aorta. J Am Heart Assoc. 2014; 3:1-11, both of which are hereby incorporated by reference. Finally, Doppler echocardiography can be used to generate a reasonable estimation of pressure, see Teien D, Karp K, Eriksson P. Non-invasive estimation of the mean pressure difference in aortic stenosis by Doppler ultrasound. Heart. 1986; 56:450-454, which is also incorporated by reference. Given the fact that surgical repair of aortic aneurysms carries a mortality rate approaching 10%, this detailed mechanical analysis would provide surgeons with complimentary data to inform their decision on whether-or-not to surgically intervene.

As presented, this technology can be directly translated in to a clinical setting as a complement to the echocardiographic analyses routinely performed on cardiovascular patients. The American Society of Echocardiography reports a complete transthoracic echocardiographic study can be reasonably expected to take between 45 and 60 minutes. While it would not be practical to add to the examination time to conduct the proposed analysis, this analysis can be completed as a post-processing step from images that are already routinely acquired. Furthermore, it is reasonable to assume an evolution of this technology which bypasses the inverse FE optimization all-together. Once this technology has been applied to enough cases, there will be a large library of evidence detailing the dynamic interplay between types of heart disease, LV geometry, regional strain, interventricular pressure, and regional stiffness. A future evolution of this technology could be developed as a form of artificial intelligence informed by a supervised machine learning algorithm to predict regional stiffness and myocardial stresses for a given patient based on the body of evidence previously collected from other patients.

Ultimately, the methods and framework proposed herein would allow for this robust mechanical analysis to be readily performed in a clinical setting for the assessment of the rate and extent of myocardial remodeling in response to heart disease. This type of point-of-care analysis has the potential to transform cardiovascular disease diagnostics and inform clinicians and researchers, alike, on patient-specific disease progression.

FIGURE LEGENDS

FIG. 1 shows formulation of a finite element mesh of the current disclosure. At both the end systole and end diastole, quantitative strain analysis was performed on LV long-axis echocardiographic images (A, D). (B, E) Epicardial, mid-myocardial, and endocardial nodes were defined from the mid-myocardial strain analysis position data and regional thickness measurements. (C, E) A eight-node trilinear hexahedral FE mesh was formulated with two elements spanning the distance between each of the mid-myocardial nodes and eight elements spanning the distance between the pairs of endocardial and epicardial nodes.

Figure 2:
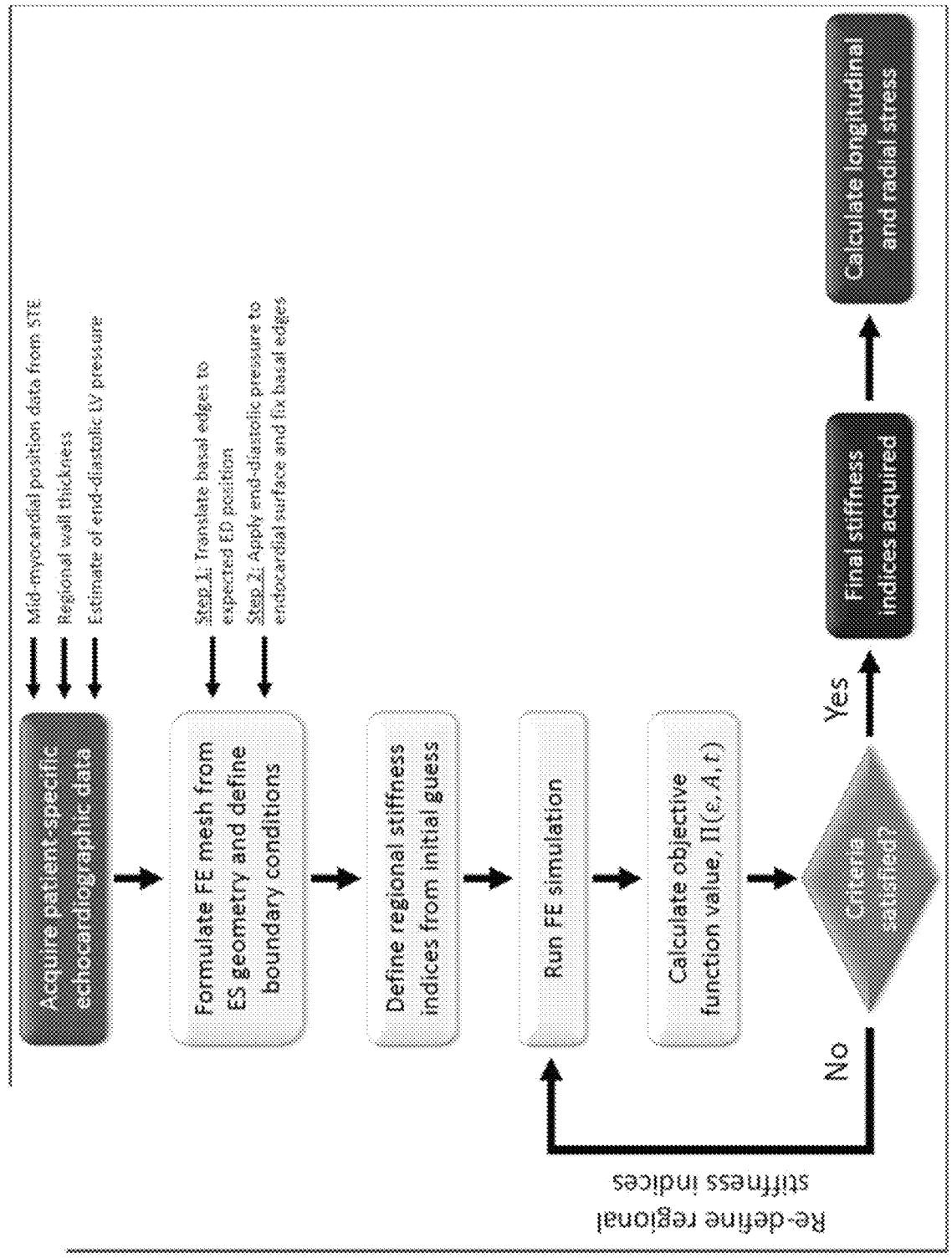
FIG. 2 shows a flowchart of the inverse methodology to identify mechanical properties from STE.

FIG. 2 shows a flowchart of the inverse methodology to identify mechanical properties from STE. From the echocardiographic cine loops, mid-myocardial position data, regional wall thickness, and estimations of PCWP were acquired. A FE model is generated from the initial end systolic geometry and boundary conditions are defined for two quasi-static simulation steps. An initial guess for the regional stiffness indices is defined and the converged solution was attained from a PARDISO linear FE solver. The objective function (Π) value is determined and evaluated against the stopping criteria. If stopping criteria is not met, regional stiffness indices were re-defined from the pattern search optimization algorithm. After the stopping criteria is satisfied, a final regional distribution of stiffness indices is acquired, and end-diastolic longitudinal and radial stress are calculated.

Figure 3:
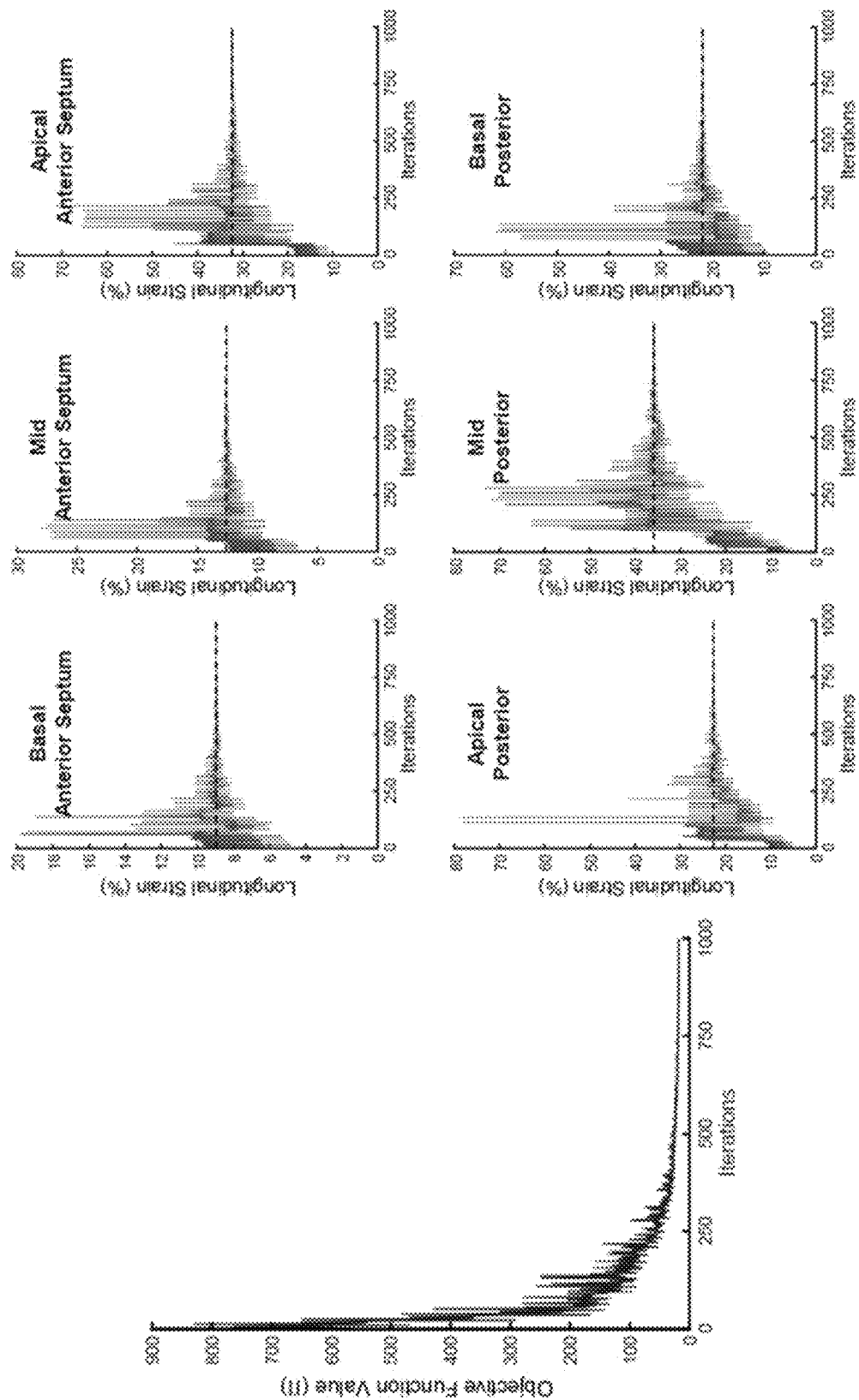
FIG. 3 shows a pattern search optimization algorithm, ideal for the minimization of a non-differentiable objective function, employed to identify an optimal set of stiffness indices coincident with the global minimum of the objective function.

FIG. 3 shows minimization of the objective function. The pattern search optimization algorithm iteratively explored combinations of regional stiffness indices until a minimum value of the objective function (Π) was attained (left). As the objective function is minimized, the regional strain computed from the FE model converged upon the experimentally measured regional strain (right).

FIG. 4 shows a representative result for a human hypertrophic left ventricle. Transthoracic echocardiographic images were obtained for a human subject presenting with a hypertrophic left ventricle and a documented history of hypertension. A normal ejection fraction (64%), elevated PCWP (16.6 mmHg), and moderately enlarged left atrium (31.3 cm$^2$) were observed. Quantitative strain analysis was performed, a FE element mesh was generated from the end systolic geometry (A), and the inverse method of identifying mechanical properties was applied to identify a distribution of stiffness indices (B). Post-processing of the FE results allows for the calculation of regional longitudinal (C) and radial (D) stress at end-diastole.

This methodological process of the current disclosure may be compiled within a novel software application termed Cardiac iPE which may be used to demonstrate the process of defining patient-specific data, formulation of a FE mesh, defining an initial guess for stiffness indices, and attaining an optimal solution through minimization of the objective function.

There are currently no products, services, or processes that can provide this type of mechanical analysis. Ultimately, the stiffness indices the current disclosure may generate will provide information about the regional mechanical properties of the myocardium without a dependence on hemodynamics or geometry. The current disclosure will provide clinicians with a diagnostic advantage as they look to assess the progression of heart disease and/or the effectiveness of treatment strategies.

Additions from White Paper

Left ventricular (LV) remodeling is a critical process underlying heart failure (HF) development and progression. While LV global longitudinal strain determined by speckle-tracking echocardiography (STE) provides a promising basis to monitor LV remodeling, reported strain measures are limited by the masking of regional differences and a dependency on hemodynamic load. The inventors extend two-dimensional STE to quantify the regional passive mechanical properties of the LV myocardium—providing clinically accessible and load-independent response variables that directly reflect the LV remodeling process.

An inverse finite element analysis was employed with a pattern search optimization algorithm to identify regional indices of passive LV myocardial stiffness based on STE-derived regional LV longitudinal strains and wall geometries. The inventors' framework was applied in two distinct porcine models of early LV remodeling, specifically following myocardial infarction and onset of LV pressure overload. The inventors track regional and temporal changes in indices of passive LV myocardial stiffness, which show enhanced early sensitivity as compared to LV global longitudinal strain and strong correlation with conventional indices of LV remodeling. The inventors' findings suggest that passive LV myocardial stiffness can be readily determined and monitored in a clinical setting, with potential to aid in HF diagnosis and prognosis.

Regional and temporal changes in computed indices of passive LV myocardial stiffness correlate with conventional indices of LV remodeling and show enhanced early sensitivity as compared to LV global longitudinal strain. The inventors' findings suggest that STE-integrated computational modeling can be used to track indices of passive LV myocardial stiffness, and thus is a potential tool for HF diagnosis and prognosis.

The objective of the current disclosure is to extend STE-based measurements to quantify LV myocardial mechanical properties and more effectively leverage the full field of speckle data to assess LV remodeling. To this end, the inventors integrate STE-derived measures of regional LV geometry and myocardial strain along with an estimation of the mechanical load (i.e. ventricular pressure) within an inverse finite-element framework to compute regional passive LV myocardial mechanical properties. STE data from porcine models of both ischemia reperfusion and LV pressure overload are processed in the inventors' inverse framework to generate spatiotemporal maps of a passive myocardial stiffness index and the diastolic myocardial stress throughout early LV remodeling.

Materials and Methods

Large Animal Models of HFrEF and HFpEF

For both models of LV failure, mature pigs (Yorkshire, 20-22 kg) were utilized whereby HFrEF was induced by intracoronary induction of ischemia-reperfusion while HFpEF was induced by LV pressure overload due to progressive ascending aortic stenosis. Briefly, for the HFrEF protocol, the pigs (n=8) were anesthetized (isoflurane, 3%/1.5 L/min; nitrous oxide, 0.5 L/min) and an angioplasty balloon catheter (5F Launcher guiding catheter, 0.058-in. HIS, Medtronic, Minneapolis, Minn.) was placed within the left anterior descending artery, immediately below the first obtuse marginal branch, under fluoroscopic guidance (Arcadis Varic C-Arm, Siemens, Munich, DE).

After 90 minutes of coronary occlusion, the balloon was deflated and the catheter system was removed. This approach resulted in a reproducible apical anterior myocardial infarction, and over time a reduction in LV ejection fraction (LVEF)—thus recapitulating the HFrEF phenotype. For HFpEF induced by LV pressure overload, pigs (n=9) were anesthetized as described supra, and the ascending aorta accessed through a left thoracotomy. An inflatable silastic vascular cuff (12 mm, Access Technologies, Skokie, Ill.) was secured around the supracoronary ascending aorta and connected to a subcutaneous access port. Serial hydraulic-mediated cuff inflation was initiated following a one-week recovery period, in which the cuff was inflated through the access port (via 0.45 mL glycerol) to achieve a specific target gradient of 75 mmHg across the cuff and induce LV pressure overload. At weekly intervals thereafter, the cuff was further inflated (0.25 mL increments) to cause a stepwise increase in the pressure gradient (25 mmHg increase/inflation).

All animals were treated and cared for in accordance with the National Institutes of Health Guide for the Care and Use of Laboratory Animals (Eighth Edition. Washington, D.C.: 2011) and all experimental protocols were approved by Institutional Animal Care and Use Committees at the University of South Carolina.

Serial Echocardiographic Studies

The day before animals underwent either coronary occlusion or placement of the aortic cuff, the pigs were sedated (diazepam, 200 mg), placed in a custom-designed sling, and transthoracic echocardiographic studies were performed (GE Vivid E9 with XDclear Ultrasound System; M5S (3.3 MHz, 40 FPS) transthoracic probe). Two-dimensional echocardiographic cine loops were acquired from a transthoracic right parasternal approach. The left atrium (LA) and LV were imaged in both the short- and long-axis views. Pulse-wave and tissue Doppler studies were performed to determine flow velocities and pressure gradients.

The pigs were then returned to the laboratory for follow-up imaging studies under identical conditions and approaches, whereby the HFrEF pigs were returned for imaging studies at 14 and 28 days post-coronary occlusion and the HFpEF pigs were returned to the laboratory at 7, 14, 21, and 28 days for both imaging studies and serial hydraulic-mediated expansion of the aortic cuff under echocardiographic guidance and sterile conditions as described previously.

Post-Acquisition Analysis of LV Function and Geometry

The digital echocardiographic images were transferred to a workstation for offline analysis (EchoPac, Vingmed, GE). LV end-diastolic volume (EDV) and LVEF were calculated using the biplane method of disks. LA area was determined from the anteroposterior dimensions acquired from the parasternal long axis view. For each digital loop, a region of interest (ROI) was defined at the onset of the R-wave by manually identifying the endocardial and epicardial borders. The ROI was then discretized with a spatial mesh of acoustic clusters to be tracked on a frame-to-frame basis throughout a single cardiac cycle. Quantitative strain analysis (Q-analysis) was performed, regional tracking quality was assessed, and the ROI was manually adjusted by the operator to improve tracking quality where necessary. Successful tracking of the ROI allowed for the definition of segmental lengths which were computed at end-diastole (L0) and continuously throughout the cardiac cycle (L). Segmental strains (ε) were then computed as:

$$\varepsilon = \frac{L - L_0}{L_0} = \frac{\Delta L}{L_0}, \quad (7)$$

where the reference length refers to the end-to-end length in the longitudinal direction of a particular echocardiographic segment (i.e. basal posterior, mid posterior, apical posterior, apical anterior septum, mid anterior septum, or basal anterior septum) or, in the case of global longitudinal strain, the end-to-end length of the mid-myocardium in the longitudinal direction (i.e. from the basal posterior, to the apex, and then to the basal anterior septum).

Subsequently, spatial coordinates of the mid-myocardial nodes were exported for each frame of the digital loop. Additionally, wall thickness was measured with the built-in caliper tool at the onset of diastole and end-diastole for each of the six conventional echocardiographic segments. Pulmonary capillary wedge pressure (PCWP) was calculated using the method proposed by Nagueh et al in 1997. Nagueh S F, Middleton K J, Kopelen H A, Zoghbi W A, Quinones M A. *Doppler tissue imaging: A noninvasive technique for evaluation of left ventricular relaxation and estimation of filling pressures.* J Am Coll Cardiol. 1997; 30:1527-33.

Formulation of the Finite-Element Mesh

Figure 5A:
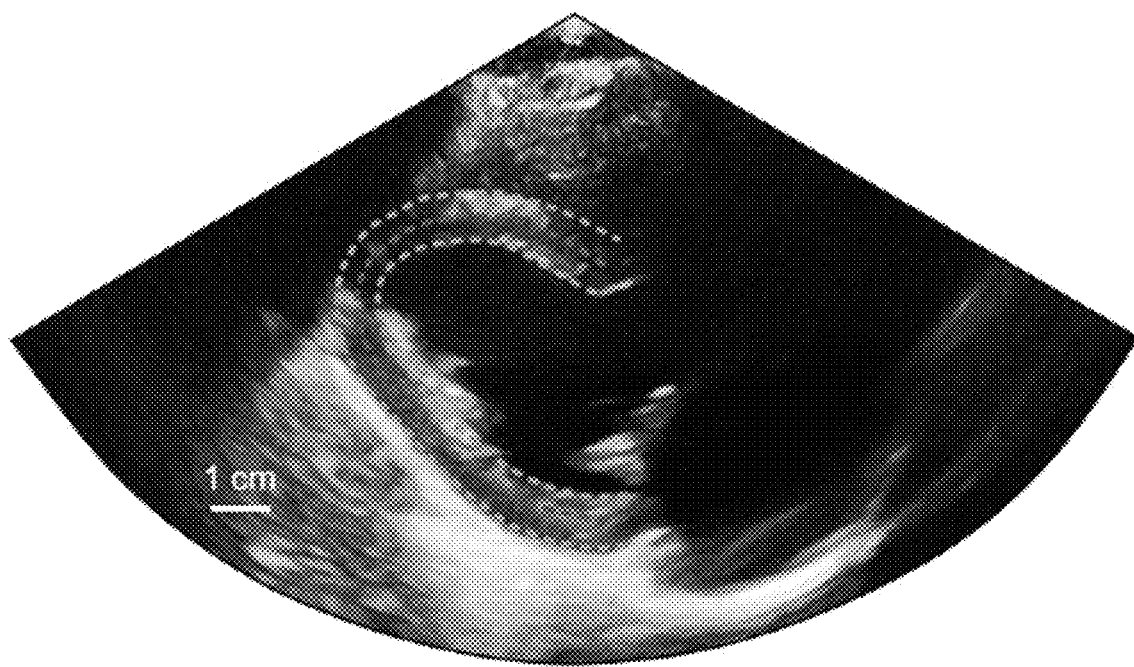
FIG. 5A shows end-systole quantitative strain analysis performed on LV long-axis echocardiographic images.
Figure 5B:
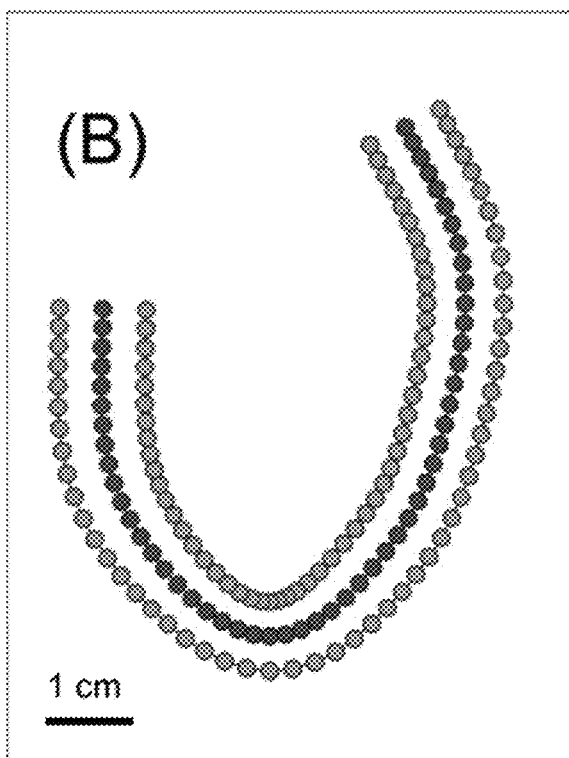
FIG. 5B shows epicardial, mid-myocardial, and endocardial nodes defined from the mid-myocardial strain analysis position data and regional thickness measurements.
Figure 5C:
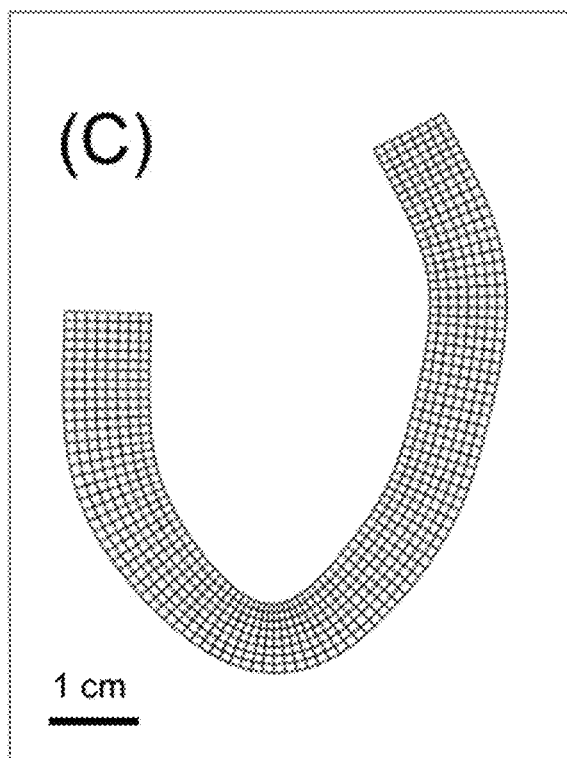
FIG. 5C shows a mesh developed from FIG. 5B.
Figure 5D:
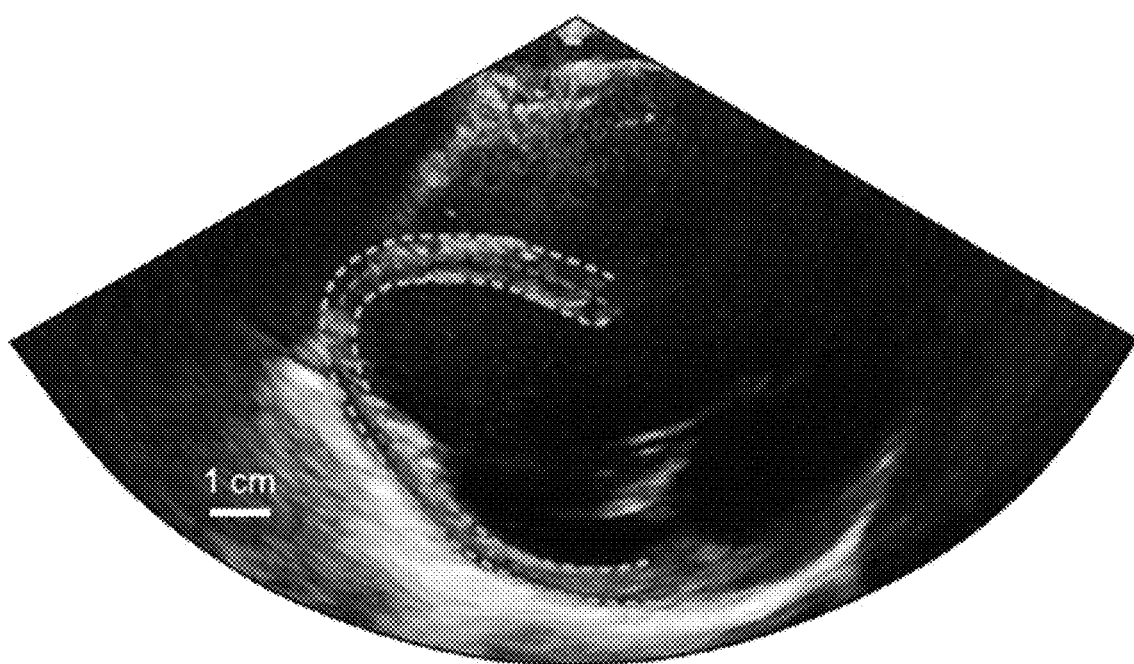
FIG. 5D shows end-diastole, quantitative strain analysis performed on LV long-axis echocardiographic images.
Figure 5E:
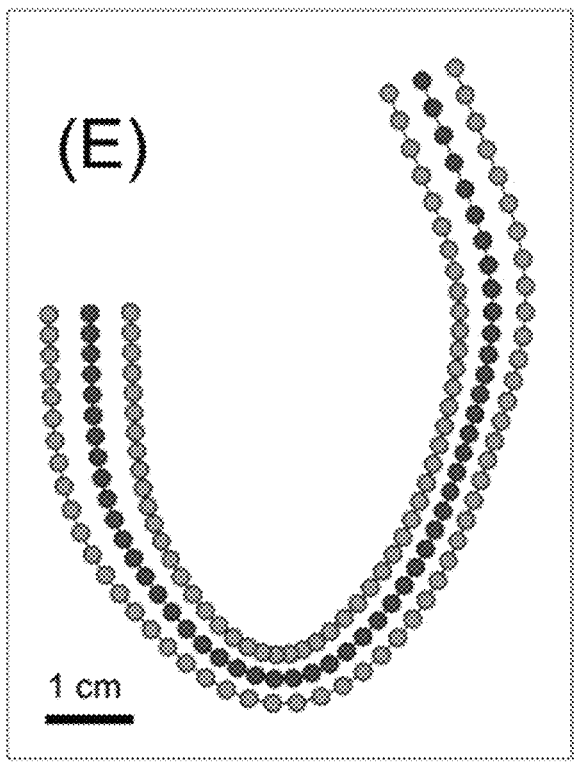
FIG. 5E shows another set of epicardial, mid-myocardial, and endocardial nodes defined from the mid-myocardial strain analysis position data and regional thickness measurements.
Figure 5F:
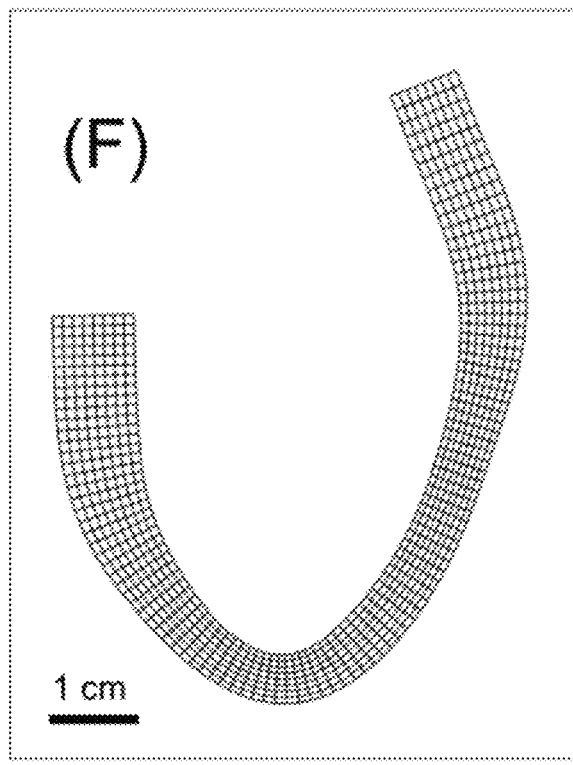
FIG. 5F shows a mesh developed from FIG. 5E.

The reference LV configuration was generated from the position of the mid-myocardial nodes at the onset of diastole, the point at which the cross-sectional area was at a minimum. For each mid-myocardial node, a wall thickness was defined by computing a cubic spline interpolation between the known wall thickness at the onset of diastole of the six echocardiographic segments. Endocardial and epicardial nodes were subsequently generated based on the position of the mid-myocardial nodes and estimated wall thicknesses. The finite-element mesh was constructed from this reference geometry composed of a monolayer of eight-node trilinear hexahedral elements with two elements spanning the distance between each of the mid-myocardial nodes and eight elements spanning the distance between the pairs of endocardial and epicardial nodes (FIGS. 5A-5C). This process was also completed for the end-diastolic configuration to enable calculation of the objective function as detailed below (FIGS. 5D-5F).

FIG. 5: Formulation of the finite element mesh. FIGS. 5A, 5D) At both end-systole and end-diastole, quantitative strain analysis was performed on LV long-axis echocardiographic images. FIGS. 5B, 5E Epicardial, mid-myocardial, and endocardial nodes were defined from the mid-myocardial strain analysis position data and regional thickness measurements. FIGS. 5C, 5F A eight-node trilinear hexahedral FE mesh was formulated with two elements spanning the distance between each of the mid-myocardial nodes and eight elements spanning the distance between the pairs of endocardial and epicardial nodes.

Material Model and Boundary Conditions

The LV myocardium was modeled as a transversely isotropic Mooney-Rivlin solid, a model well-suited for biological soft tissues with a preferred fiber direction. The uncoupled strain energy function is:

$$W = F_1(\tilde{I}_1, \tilde{I}_2) + F_2(\tilde{\lambda}) + \frac{K}{2}[\ln(J)]^2, \quad (8)$$

where K is the bulk modulus-like penalty parameter and J is the determinant of the deformation gradient tensor. The function $F_1(\tilde{I}_1, \tilde{I}_2)$, a function of the first and second invariants of the deviatoric right Cauchy-Green deformation tensor, represents the material response of the isotropic Mooney-Rivlin ground substance matrix of the form:

$$F_1(\tilde{I}_1, \tilde{I}_2) = S[C_1(\tilde{I}_1 - 3)] + S[C_2(\tilde{I}_2 - 3)] + \frac{K}{2}[\ln(J)]^2 \quad (9)$$

where $C_1$ and $C_2$ are the material coefficients and S is the regional stiffness index. $F_2(\tilde{\lambda})$, a function of the fiber stretch ratio, represents the contribution from the fiber family with a strain energy of the following form:

$$F_2(\tilde{\lambda}) = \begin{cases} 0 & \tilde{\lambda} \leq 1 \\ C_3\left[e^{-C_4}(Ei(C_4\tilde{\lambda}) - Ei(C_4)) - \ln\tilde{\lambda}\right] & 1 < \tilde{\lambda} < \lambda_m \\ C_5(\tilde{\lambda} - 1) + C_6\ln\tilde{\lambda} & \tilde{\lambda} \geq \lambda_m \end{cases} \quad (10)$$

where $C_3$ scales the exponential term, $C_4$ is the fiber crimping coefficient, $C_5$ is the modulus of the straightened fibers, and $\lambda_m$ is the stretch at which the fibers are straightened. Furthermore, $Ei(\cdot)$ is the exponential integral function and $C_6$ is determined from stress continuity requirements. The fiber orientation was specified for each element to be 15° relative to the longitudinal axis on the longitudinal-radial plane, and $\lambda_m$ was assigned to be 1.10. The remaining material parameters, barring the regional stiffness index, were valued in accordance with prior work on biaxial testing on excised canine hearts. The regional stiffness index, S, was determined from the optimization scheme described in the following section.

Two quasi-static structural mechanics steps were defined as follows. In step one, a prescribed translation was applied to the basal nodes from the reference configuration to the expected position at end-diastole as determined from STE. In step two, the basal node positions were fixed, and the end-diastolic pressure was applied to the endocardial surface. To mimic the tethering effects of the right ventricle and the pericardium, an opposing pressure was applied to the basal and mid-ventricular epicardial nodes with a magnitude of 25% of that of the interventricular pressure. The solution was computed using the PARDISO linear solver within the FEBio application.

Identification of Material Properties

An objective function (Π) of the form:

$$\Pi = \left( \frac{A' - A}{A} + \sum_{i=1}^{6} \left( \frac{\varepsilon'_i - \varepsilon_i}{\varepsilon_i} \right) + \frac{\bar{t}' - \bar{t}}{\bar{t}} \right) \times 100\% \quad (11)$$

was developed as a function of the actual end-diastolic area (A), regional strain (εi) relative to the reference mesh, and mean wall thickness ($\bar{t}$) determined from the end-diastolic mesh (FIG. 5F). Additionally, A', εi', and $\bar{t}'$ represent the end-diastolic area, regional strain relative to the undeformed mesh, and mean wall thickness computed from the deformed FE model, respectively. The factors entering the optimization scheme were the stiffness indices (S) defined at the center of each of the six conventional anatomical segments of the LV. A cubic spline interpolation was used to define a continuous distribution of stiffness indices between the six segments. A pattern search optimization algorithm, ideal for the minimization of a non-differentiable objective function, was employed to identify an optimal set of stiffness indices coincident with the global minimum of the objective function. The pattern search algorithm was terminated when a successful poll resulted in a change in the objective function of less than 1E-6, see FIG. 6.

Figure 6A:
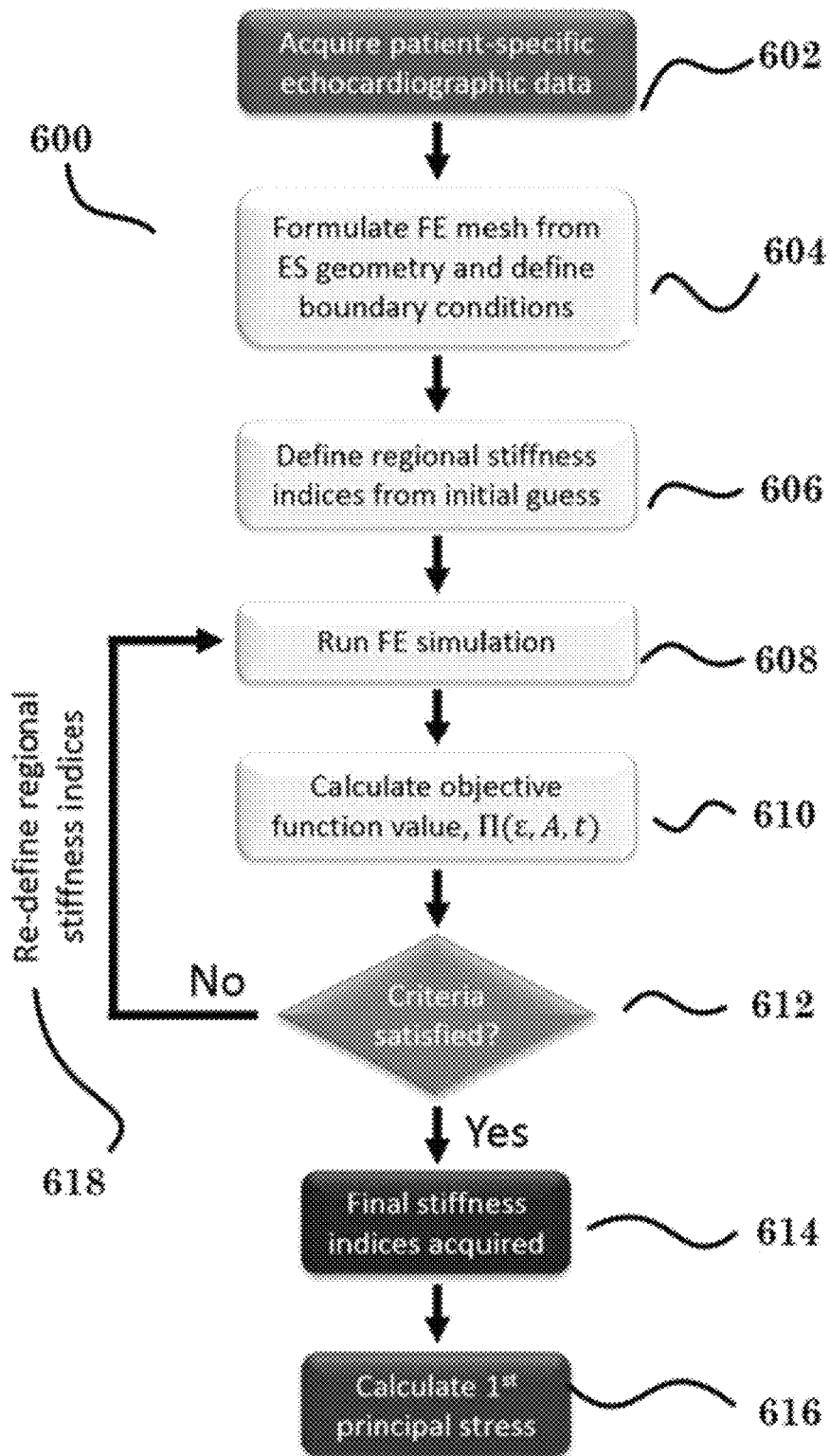
FIG. 6A shows echocardiographic cine loops, mid-myocardial position data, regional wall thickness, and estimations of PCWP.
Figure 6B:
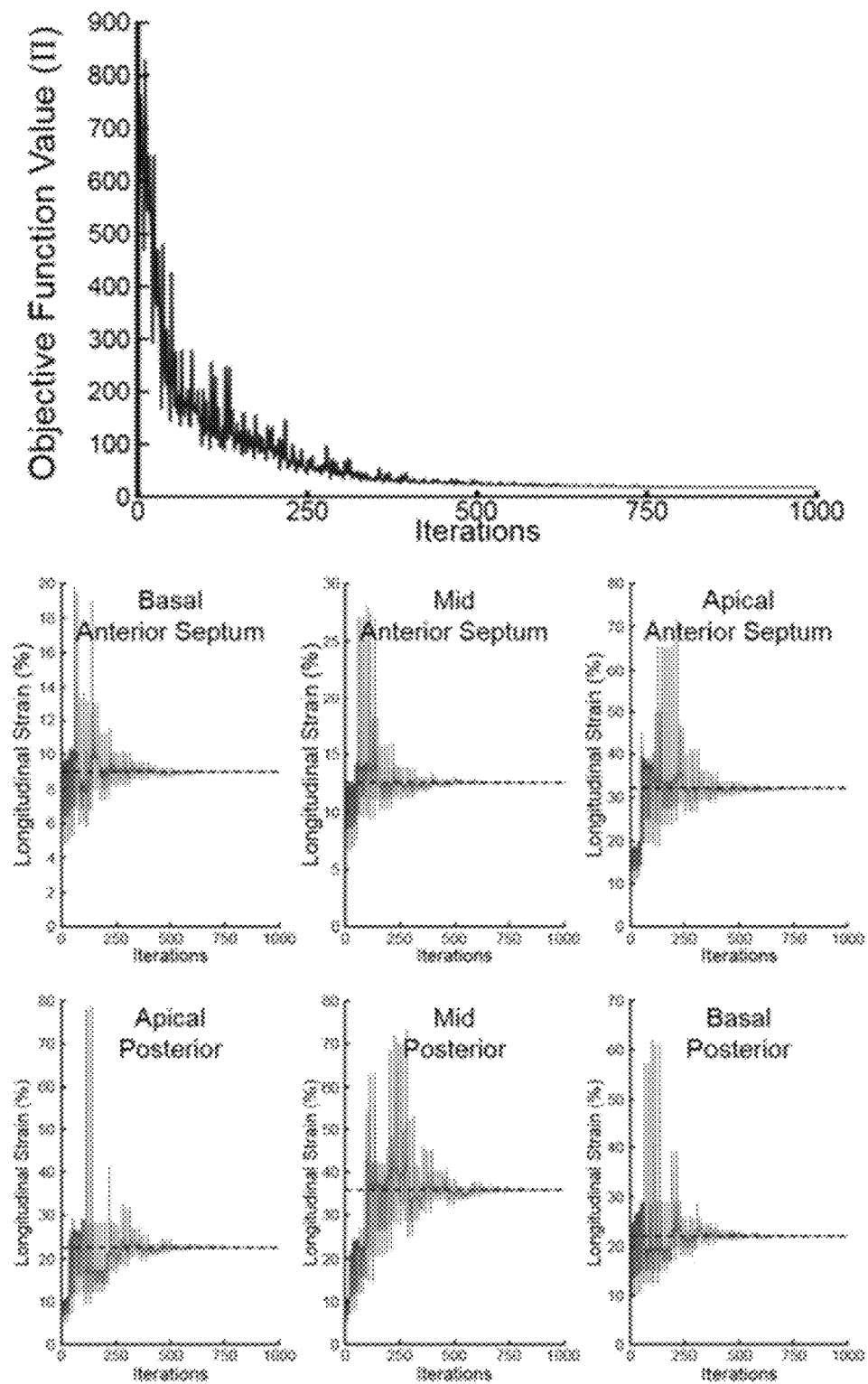
FIG. 6B shows the objective function (Π) value determined and evaluated against the stopping criteria.

FIGS. 6A and 6B—inverse methodology to identify mechanical properties from STE. FIG. 6A—from the echocardiographic cine loops, mid-myocardial position data, regional wall thickness, and estimations of PCWP were acquired. A FE model is generated from the initial end-systolic geometry and boundary conditions are defined for two quasi-static simulation steps. An initial guess/estimate for the regional stiffness indices is defined and the converged solution was attained from a PARDISO linear FE solver. FIG. 6B—the objective function (Π) value is determined and evaluated against the stopping criteria. If stopping criteria is not met, regional stiffness indices were re-defined from the pattern search optimization algorithm. After the stopping criteria is satisfied, a final regional distribution of stiffness indices is acquired, and end-diastolic longitudinal and radial stress are calculated. The pattern search optimization algorithm iteratively explored combinations of regional stiffness indices until a minimum value of the objective function (Π) was attained.

FIG. 6A also shows a method 600 of noninvasive quantification of myocardial mechanical properties 600. At step 602, patient specific echocardographic data is obtained. At step 604, FE mesh is formulated from E5 geometry and the boundary conditions are defined. At step 606, regional stiffness indices are established. At step 608, an FE simulation is run. At step 610, the object function value is calculated. At step 612, it is determined whether the criteria are satisfied. If the answer to 612 is in the affirmative, final stiffness indices are acquired at step 614 and the 1st principal stress is calculated at step 616. If the answer to step 612 is in the negative, then at step 618, the regional stiffness indices are redefined and steps 608, 601, 612, and 618 are repeated until the answer to 612 becomes that the criteria are satisfied.

As the objective function is minimized, the regional strain computed from the FE model converged upon the experimentally measured regional strain.

The optimization process was conducted on a workstation with an eight-core processor (3.7 GHz) and 32 GB of RAM. After optimization was complete, a final simulation with a refined FE mesh and assigned regional values of S was performed, thus facilitating the calculation of the first principal stress field.

Statistical Analysis

Data are reported as the mean±standard error of the mean. Comparative analyses between the two groups were performed using a two-way analysis of variance followed by pair-wise comparisons using the least significant difference post hoc study. A Pearson correlation analysis was used to interrelate classical echocardiographic indices with those derived from regional inverse analyses. A p-value of less than 0.05 was considered statistically significant. All statistical analyses were performed in MATLAB (version R2018a, The MathWorks Inc).

Results

LV Function and Geometry

LV function and geometry at baseline and at the two specified time points (14 and 28 days) are shown in Table 1, see FIG. 12. In the HFrEF group, LVEF was reduced and LV dilation occurred; consistent with the HFrEF phenotype. In the HFpEF group, LVEF and LV volume were unchanged, whereas LA area increased; consistent with the HFpEF phenotype. Spatial mapping of regional LV longitudinal strain showed an overall reduction in the HFrEF group, with the greatest reductions occurring in the mid- and apical-anterior regions. In marked contrast, regional LV longitudinal strain remained comparatively preserved in the HFpEF group (FIG. 7A). Global LV longitudinal strain fell by approximately 50% from baseline at both 14 and 28 days in the HFrEF group, whereas there was no change in the HFpEF group (FIG. 7B). The relative heterogeneity of LV strain, reflected by the coefficient of variation among regional strains, more than doubled in the HFrEF group by 28 days but remained unchanged in the HFpEF group (FIG. 7B).

Figure 7:
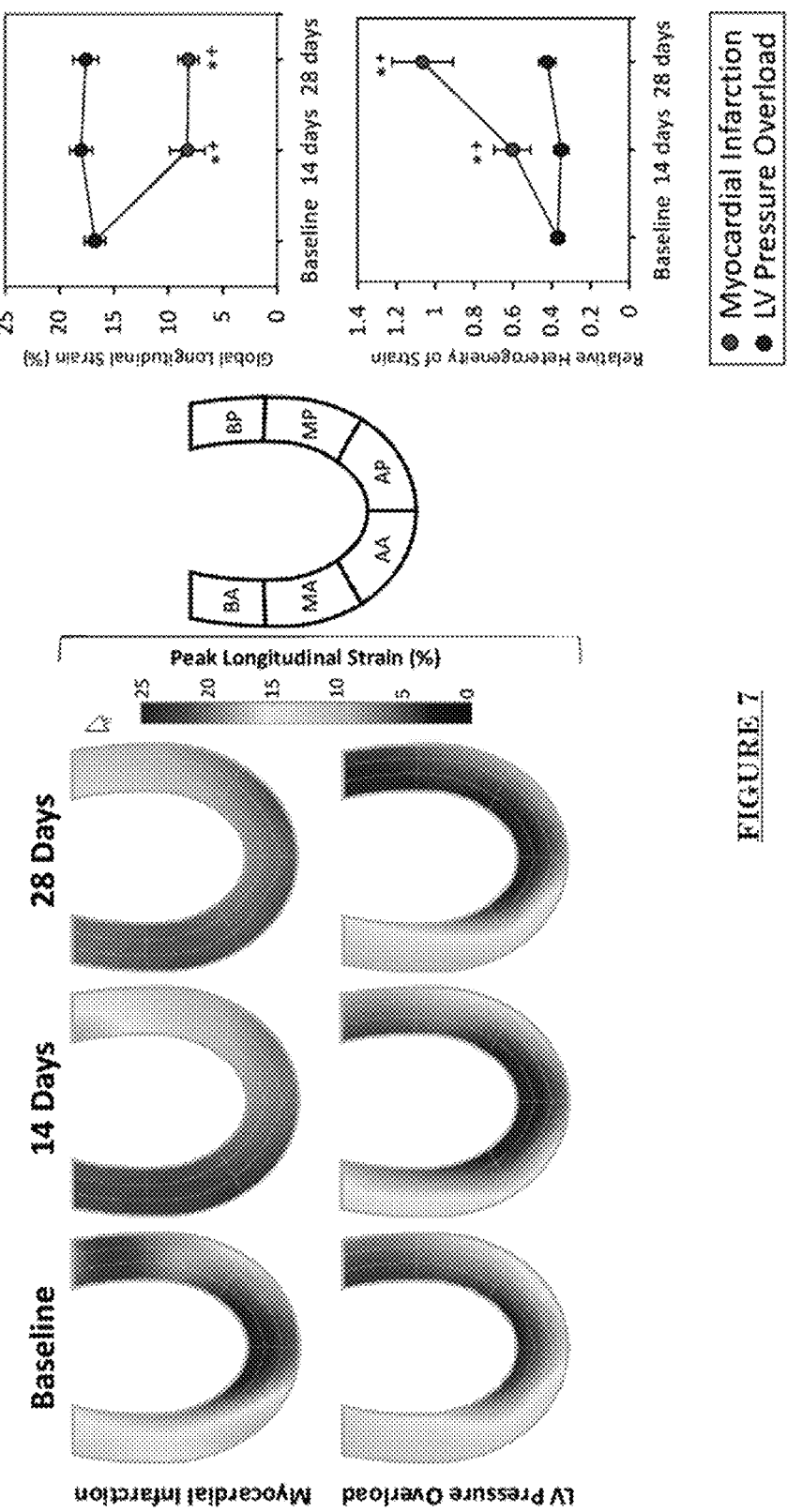
FIG. 7 shows changes in peak longitudinal strain throughout disease progression.

FIG. 7: Changes in peak longitudinal strain throughout disease progression. (A) Spatial maps of the absolute value of the peak LV longitudinal segmental strain determined directly from quantitative STE were generated for each of the two study groups at baseline as well as 14 and 28 days after the onset of disease. (B) The global LV longitudinal strain, taken as the fractional change in the total length of the LV cross-section, was determined for each subject over time. The relative heterogeneity of strain, taken as the coefficient of variation between each of the regional measurements, was determined for each subject over time. * $p<0.05$ vs. respective baseline value; +$p<0.05$ vs. respective HFpEF value.

Inverse Estimation of Regional LV Myocardial Stiffness Indices

For each case, the pattern search optimization algorithm was initiated, and the relative error in regional strain, mean wall thickness, and LV area was quantified through the objective function ($\Pi$) for each set of stiffness indices defined by the algorithm. A global minimum of the objective function was reached through iterative refinement of the stiffness indices for all cases with an average convergence time of 48.6±3.4 minutes. The minimum objective function values obtained for the HFrEF group at both 14 days and 28 days were found to be significantly elevated relative to baseline values ($\Pi=11.8\pm1.4$ (baseline) vs. $\Pi=28.3\pm7.7$ (14 days) and $\Pi=35.3\pm6.9$ (28 days), $p<0.05$). In contrast, insignificant changes in the obtained minimum objective function values were observed in the HFpEF group between baseline and 28 days. Elevated objective function values in the HFrEF group are an expected consequence of the increasingly heterogeneous wall geometry and mechanical behavior associated with the induced LV remodeling.

Changes in LV myocardial passive stiffness of the HFrEF group exhibited obvious regional dependence, exemplified at 28 days by the nearly order-of-magnitude higher stiffness index in the infarcted apical anterior region as compared to the remote myocardium (80.6±14.9 vs. 8.6±2.7) (FIG. 8A). The global stiffness index, defined as the spatial-average of the passive regional stiffness indices, reached a maximum at 14 days in the HFrEF group and remained elevated relative to baseline at 28 days (FIG. 8B). While changes in the global stiffness index in the HFpEF group were attenuated in comparison to the HFrEF group, a greater than three-fold increase relative to baseline was observed at 28 days. The relative heterogeneity of stiffness, taken as the coefficient of variation among regional stiffness indices, was significantly elevated in the HFrEF group relative to both baseline and the HFpEF group at both 14 and 28 days (FIG. 8B).

Figure 8:
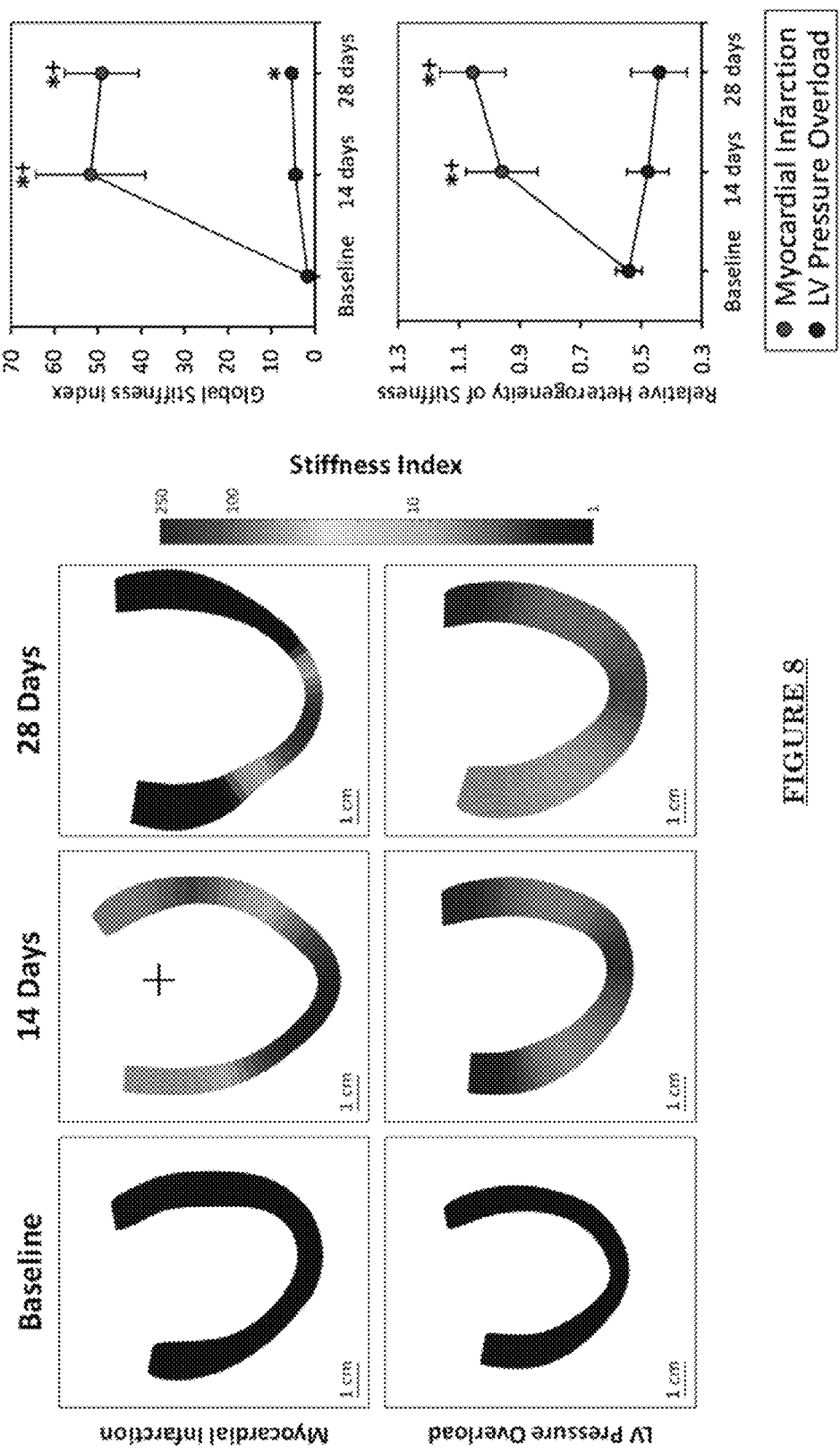
FIG. 8 shows dynamic changes in the regional mechanical stiffness index throughout disease progression.

FIG. 8: Dynamic changes in the regional mechanical stiffness index throughout disease progression. The inverse method of identifying mechanical properties was applied to each subject at baseline as well as 14 and 28 days after the onset of disease. (A) Representative cases of both heart disease models demonstrate heterogeneous regional changes in mechanical stiffness as the disease progresses. (B) The spatially-averaged global stiffness index was determined for each subject over time. Additionally, the relative heterogeneity of stiffness, taken as the coefficient of variation for each subject, was determined for each subject over time. * $p<0.05$ vs. respective baseline value; +$p<0.05$ vs. respective HFpEF value.

LV Myocardial Wall Stress

Subsequent simulations that incorporate the identified local stiffness indices allowed for quantification of the 1st principal stress field at end-diastole. At both 14 and 28 days, the maximal regional stress observed in the HFrEF group was coincident with the location of the ischemic injury, while a qualitatively more uniform stress distribution was observed in the HFpEF group (FIG. 5A). The global $1^{st}$ principal stress, defined as the spatial-average of $1^{st}$ principal stress, was elevated relative to baseline in both groups at 14 and 28 days, with significantly higher stresses in the HFrEF group compared to the HFpEF group (FIG. 5B).

Figure 9:
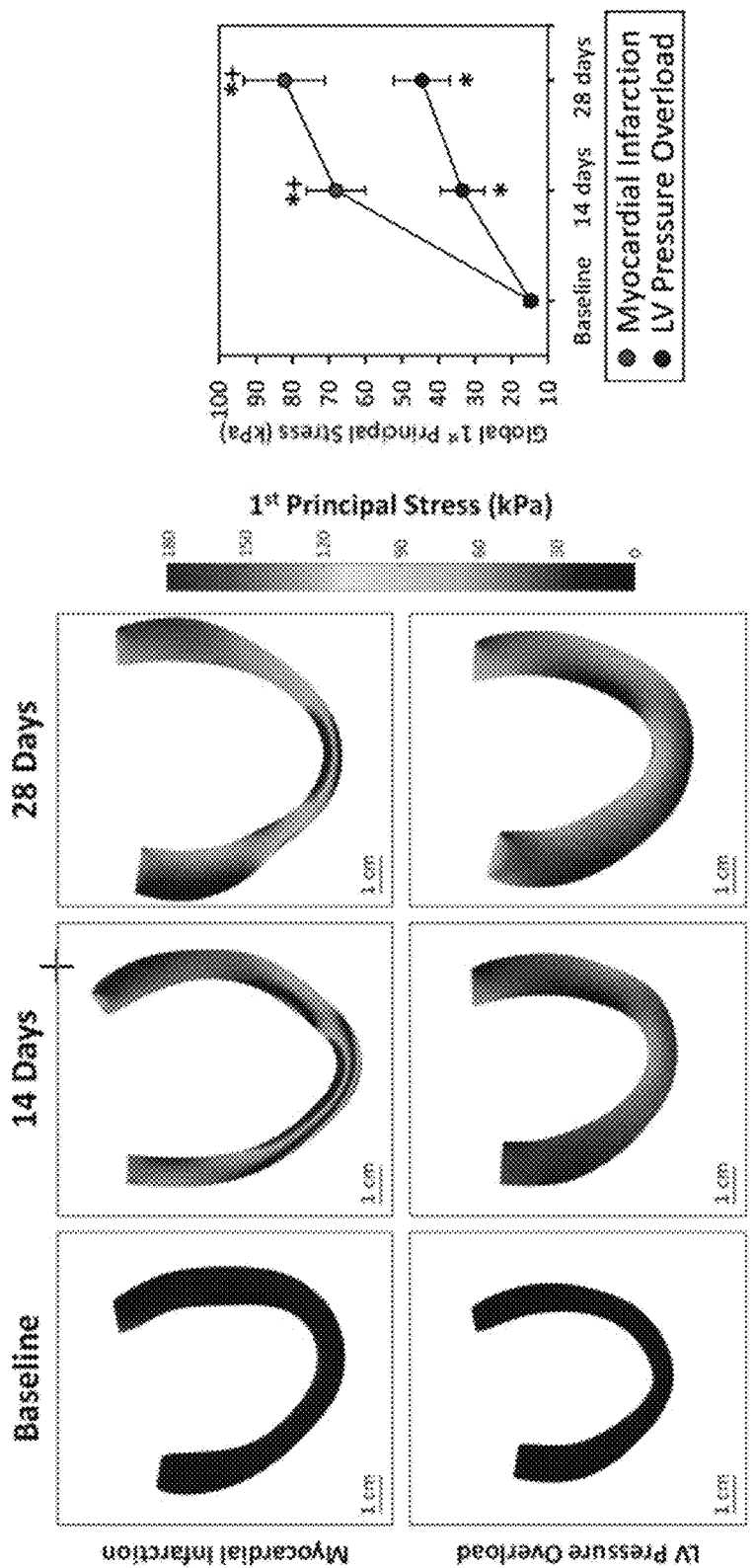
FIG. 9 shows the determination of end-diastolic myocardial wall stress.

FIG. 9: Determination of end-diastolic myocardial wall stress. The $1^{st}$ principal stress throughout the myocardium was computed for each subject at baseline as well as 14 and 28 days after the onset of disease. (A) Representative cases of both heart disease models demonstrate the spatial variance of $1^{st}$ principal stress and the extent to which this is altered throughout the progression of the disease. (B) The spatial-average of $1^{st}$ principal stress (i.e. global $1^{st}$ principal stress) was determined for each subject over time. * $p<0.05$ vs. respective baseline value; +$p<0.05$ vs. respective HFpEF value.

Correlation Analysis

Figure 10:
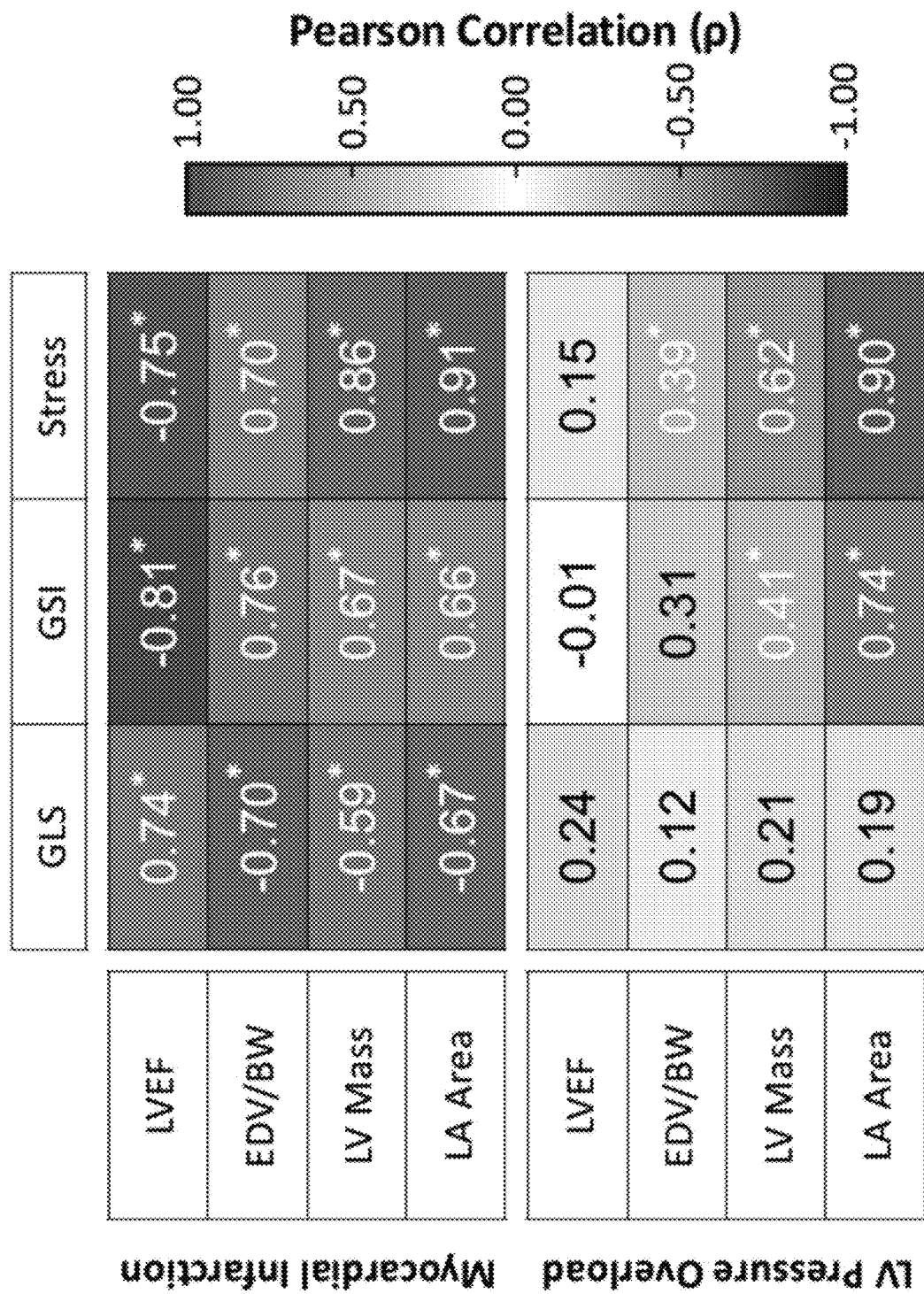
FIG. 10 shows a Pearson correlation used to interrelate standard echocardiographic response variables (LVEF, EDV/BW, and LA Area) with patient-matched changes in biomechanical response variables (GLS, GSI, and Stress).

A correlation matrix was developed for each group to relate established indices of global function and geometry to computed biomechanical indices (FIG. 10). In the HFrEF group, LV global longitudinal strain positively correlated with LVEF and negatively correlated with LV volume and LA area. Inverse relations were observed when these indices were correlated with global stiffness index and global 1st principal stress. Conversely in the HFpEF group, there was no correlation between LV global longitudinal strain and LV ejection fraction, volume, or LA area. Notably, LA area, an index of progressive HF, exhibited strong positive correlations with the computed global stiffness index and global $1^{st}$ principal stress in both the HFrEF and HFpEF groups.

FIG. 10: Correlation between biomechanics and global indices of geometry and function. A Pearson correlation was used to interrelate standard echocardiographic response variables (LVEF, EDV/BW, and LA Area) with patient-matched changes in biomechanical response variables (GLS, GSI, and Stress) in each disease model. * $p<0.05$ for the Pearson correlation coefficient (ρ). (LVEF: left ventricular ejection fraction; EDV: end-diastolic volume; BW: body weight; LA: left atrium; GLS: global LV longitudinal strain; GSI: global stiffness index; Stress: spatial-average of 1st principal stress)

Discussion

The structural and functional milestones for the development and progression to heart failure (HF) are changes in LV structure and function—commonly termed LV remodeling. This process is manifested at the regional LV myocardial level, and thus, approaches which can identify and be sensitive to changes in regional LV myocardial mechanics would allow for early detection in patients at risk for HF progression.

While past studies using magnetic resonance imaging and post-processing algorithms have identified the potential relevance of assessing regional mechanics in patients with developing HF, this approach can be problematic. Firstly, this imaging approach is not amenable to point-of-care application and analysis. Secondly, this imaging approach is not readily amenable to repeated, serial measurements in terms of screening and identifying HF progression. Accordingly, the major significance of this disclosure was to put-to-practice a methodology and framework to quantify LV myocardial mechanical properties based on post-processing of typically available echocardiographic data.

While HF is a term which applies to the spectrum of symptoms, it is important to phenotype the underlying HF process. In that regard, it is now recognized by consensus that HFrEF and HFpEF are two distinct phenotypes, with differing etiologies, trajectories to HF, and, most importantly, distinctly different forms of LV dysfunction. To that end, the inventors developed a novel approach to quantify LV myocardial mechanical properties and applied it to relevant large animal models of HFrEF and HFpEF. The inventors results demonstrated the utility of this approach in terms of serial measurements and revealed distinctly different patterns of regional LV myocardial mechanical changes in HFrEF and HFpEF. This work underscores the need for sensitive assessments of LV regional mechanical performance/properties to identify the development and progression of these HF phenotypes.

Even though the present disclosure developed a regional LV stiffness index which is unique, relative comparisons to other studies can be made. Specifically, elevations in the LV stiffness index with HFrEF, which peaked at 14 days post-MI, reflect similar trends in mechanical property indices reported in both in-vivo and ex-vivo studies. Furthermore, the more progressive increases in this LV stiffness index with HFpEF is in agreement with observations made in both small and large animal models of LV pressure overload-induced hypertrophy.

However, it should be emphasized that the increased LV stiffness index in both HFrEF and HFpEF does not imply similar biological or physiological underpinnings. Specifically, in HFrEF secondary to MI, the predominant contribution to the increased global LV stiffness index was contained within the MI regions; reflective of scar formation and collagen accumulation. Contrarily in HFpEF, the rise in LV stiffness indices was due to a more global shift; reflective of the more diffuse collagen accumulation (i.e. fibrosis). The present disclosure demonstrated that these distinctly different patterns of LV myocardial stiffness could be identified in both a spatial and temporal fashion.

Clinical Translation

Figure 11A:
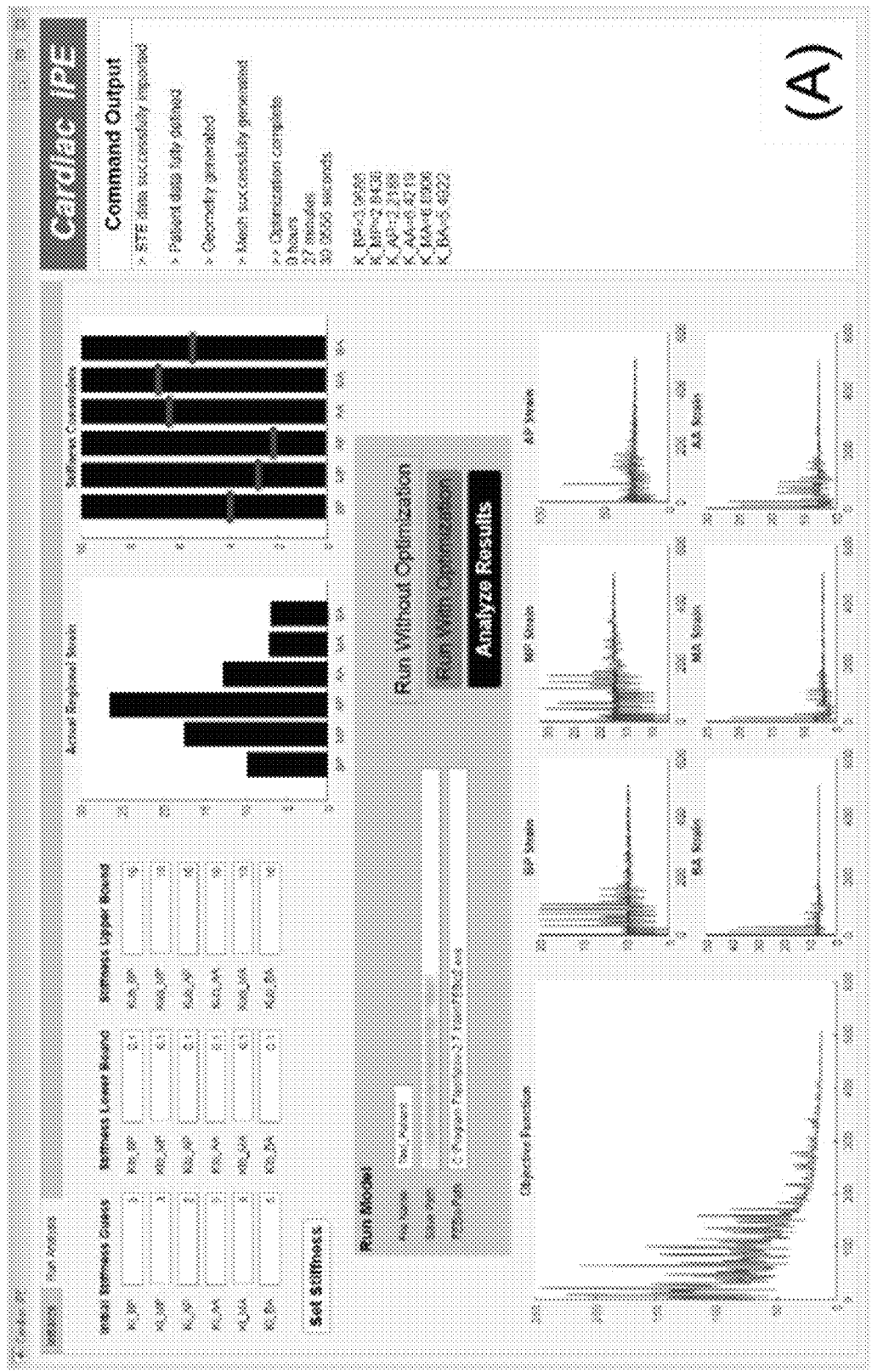
FIG. 11A shows the methodological process compiled within a novel software application designed for clinical use and applied on transthoracic echocardiographic images obtained from a human subject.

The approaches applied to these preclinical large-animal models were then put-to-practice in terms of deployment as a complete software application, FIG. 11A, using a de-identified transthoracic echocardiographic study (privacy policies set forth by the Department of Veteran's Affairs Cooperative Studies) of a patient with defined HFpEF (i.e. elevated LV filling pressure and LA enlargement). Using the methodological approaches described herein, the heterogeneous distributions of stiffness indices and $1^{st}$ principal Cauchy stress were computed, FIGS. 11B-11D. As presented, this technology can be directly translated into a clinical setting as a complement to current standard-of-care echocardiography studies.

Figures 11B, 11C, 11D:
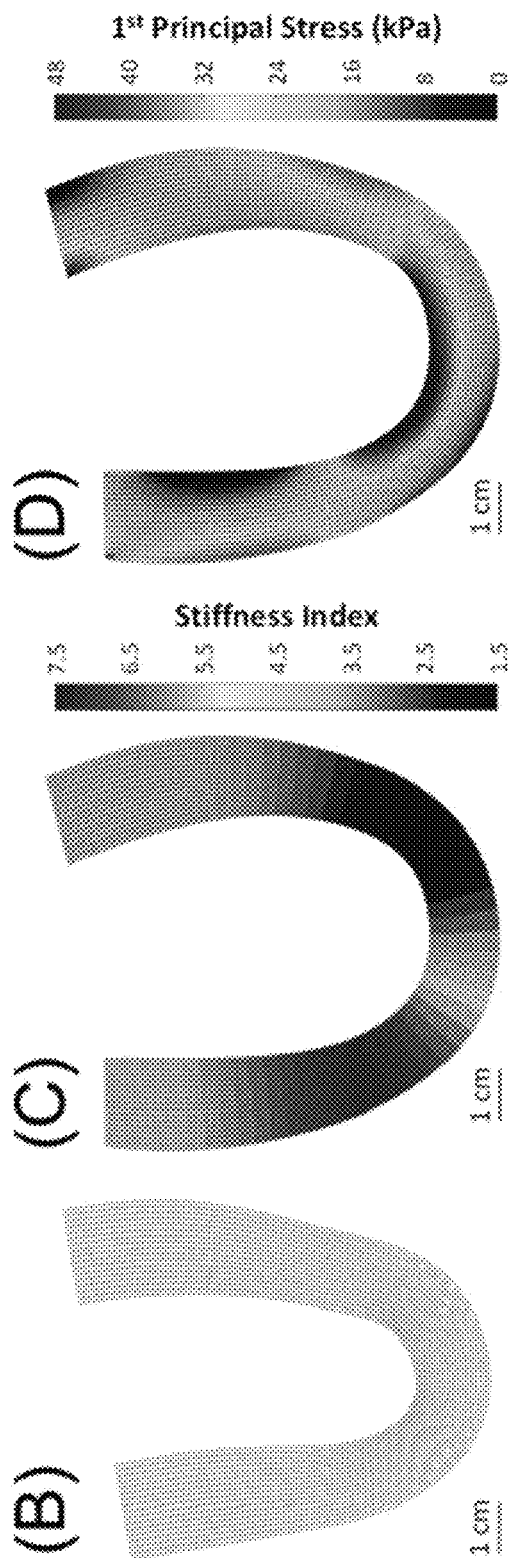
FIG. 11B shows a FE mesh was generated from the end-systolic geometry.
FIG. 11C shows the inverse method of identifying mechanical properties to identify a distribution of stiffness indices.
FIG. 11D shows post-processing of the FE results allows for the calculation of first principal stress at end-diastole.

FIG. 11 Clinical translation of methodology. FIG. 11A This methodological process was compiled within a novel software application designed for clinical use and applied on transthoracic echocardiographic images obtained from a human subject. Quantitative strain analysis was performed, FIG. 11B a FE mesh was generated from the end-systolic geometry, and FIG. 11C the inverse method of identifying mechanical properties was applied to identify a distribution of stiffness indices. FIG. 11D Post-processing of the FE results allows for the calculation of first principal stress at end-diastole.

Future Directions

While this proof-of-concept disclosure was completed on a workstation as a post-processing step for previously acquired images, it is feasible to translate this methodology to a server or cloud-computing framework to allow for direct incorporation into standard echocardiography machines. The FE solver and optimization algorithm employed in this disclosure utilize parallelization of computational cores. Therefore, incorporating this framework into a many-threaded computational platform will drastically improve computational time—increasing the likelihood of translating this analysis in a clinical setting. Furthermore, it is reasonable to assume an evolution of this technology which bypasses the inverse FE optimization all-together. Once this technology has been applied to enough cases, there will be a large library of evidence detailing the dynamic interplay between regional passive mechanical property changes and various forms of heart disease. A future evolution of this technology could be developed as a form of artificial intelligence informed by a supervised machine learning algorithm to predict the evolution of regional myocardial stiffness and stresses for a given patient based on the body of evidence previously collected from other patients.

Methodological Limitations

The present disclosure demonstrates that an inverse methodology can be reasonably performed to estimate the passive mechanical properties of the LV myocardium relevant to a clinical context. However, several methodological limitations must be considered. First, while the inventors results are in qualitative agreement with previously reported findings, in-vivo quantification of mechanical properties should be validated against results obtained from ex-vivo mechanical testing and modeling. Furthermore, given the inherent mechanical nonlinearity of the myocardium, the resultant passive stiffness indices refer only to a specific (low pressure) component of the overall myocardial mechanical response.

In this model iteration, the inventors identify a model scaling parameter (stiffness index S) that modulates the passive mechanical behavior of only the isotropic ground substance in the Mooney-Rivlin potential function. Future model iterations that extend beyond this disclosure will seek simultaneous identification of multiple scaling parameters that act on both isotropic and anisotropic components of the overall strain energy function of the LV myocardium. Additionally, prior studies have shown shifts in the predominant collagen fiber orientation and undulation as a consequence of disease progression and relative position in the LV. While this disclosure assumes a constant fiber angle on the longitudinal-radial plane and a constant degree of fiber undulation, future iterations of the model will incorporate these known variations. Finally, the model is limited to two-dimensions and exhibits sensitivity to the applied boundary conditions. Future work will be focused on translating this framework to three-dimensions and the application of increasingly realistic boundary conditions.

The methods and framework proposed herein promote passive LV myocardial mechanical property identification, and therefore could help evaluate the rate and extent of LV remodeling in the context of heart disease. This type of noninvasive, point-of-care analysis has the potential to significantly improve cardiovascular disease diagnostics and inform clinicians and researchers on patient-specific disease progression.

Clinical Motivation: Heart failure is the leading cause of morbidity and mortality across the world. Left ventricular (LV) remodeling, a chronic response to myocardial injury, is a key process in the development and progression of heart failure. As such, sensitive techniques to track the rate and extent of LV remodeling are necessary to evaluate risk and treatment options on a patient-specific basis. Echocardiography has become the gold standard for assessing the structure and function of the heart. Moreover, recent advancements in both hardware and software have given rise to a relatively new echocardiographic capability: the assessment of regional myocardial deformation through two-dimensional speckle tracking echocardiography (STE). Despite the potential applications of STE, a dependency on hemodynamic load and LV geometry has diminished its widespread clinical utility.

Novel Technology: The inventors novel technology is an extension of STE that enables non-invasive quantification of the mechanical properties of the LV myocardium, potentially providing a more sensitive response variable to track the progression of LV remodeling. An inverse finite element analysis technique is employed with a pattern search optimization algorithm to identify the distribution of mechanical properties necessary to match in-silico LV strains, average wall thickness, and area with those measured in-vivo (FIG. 7). Our software therefore uses available image data to produce a spatial map of the LV myocardial mechanical properties (FIG. 8).

Clinical Application: Non-invasive quantification of the mechanical properties of the LV myocardium will compliment standard echocardiographic analysis and potentially provide a sensitive biomechanical marker of the rate and extent of LV remodeling. Furthermore, this analysis can be completed as a post-processing step from echocardiographic images that are routinely acquired in a complete transthoracic echocardiographic study. This type of point-of-care analysis has the potential to significantly improve cardiovascular disease diagnostics and inform clinicians on patient-specific disease progression.

While the present subject matter has been described in detail with respect to specific exemplary embodiments and methods thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art using the teachings disclosed herein.

What is claimed is:

1. A method for analyzing passive left ventricular myocardial stiffness comprising:
   measuring regional left ventricular geometry;
   measuring myocardial strain;
   estimating a ventricular pressure within an inverse finite-element network;
   computing regional left ventricular myocardial mechanical properties; and
   generating a spatiotemporal map;
   wherein an objective function in the form of:

$$\Pi = \left( \frac{A' - A}{A} + \sum_{i=1}^{6} \left( \frac{\varepsilon'_i - \varepsilon_i}{\varepsilon_i} \right) + \frac{\bar{t}' - \bar{t}}{\bar{t}} \right) \times 100\%.$$

is developed as a function of, at least, actual end-diastolic area (A), regional strain ($\varepsilon_i$) relative to a reference mesh, and mean wall thickness ($\bar{t}$) determined from an end-diastolic mesh.

2. The method of claim 1, wherein the spatiotemporal map illustrates passive myocardial stiffness and diastolic stress.

3. The method of claim 1, wherein left ventricular configuration is generated from a position of the mid-myocardial nodes at onset of diastole.

4. The method of claim 1, wherein at least two quasi-static structural mechanics steps are defined as follows:
   applying a prescribed translation to basal nodes from a reference configuration to an expected position at end-diastole as determined from speckle-tracking echocardiography; and
   fixing basal node positions and applying end-diastolic pressure to an endocardial surface.

5. The method of claim 4, further comprising mimicing tethering effects of a right ventricle and a pericardium by applying an opposing pressure to the basal and mid-ventricular epicardial nodes.

6. The method of claim 1, further comprising generating endocardial and epicardial nodes based on the position of the mid-myocardial nodes and estimated wall thicknesses.

7. The method of claim 6, further comprising constructing a finite element mesh from a reference geometry composed of trilinear hexahedral elements spanning a distance between each of the mid-myocardial nodes and spanning a distance between pairs of endocardial and epicardial nodes.

8. The method of claim 7, further comprising wherein a trilinear hexahedral finite element mesh is formulated with two elements spanning the distance between each mid-myocardial nodes and a distance between the pairs of endocardial and epicardial nodes.

* * * * *